United States Patent
Berger et al.

[19]

[11] Patent Number: 5,958,934
[45] Date of Patent: Sep. 28, 1999

[54] ARYL PYRIMIDINE DERIVATIVES AND USES THEREOF

[75] Inventors: Jacob Berger, Los Altos Hills; Lee Allen Flippin, Woodside; Robert Greenhouse, Newark; Saul Jaime-Figueroa, Fremont; Yanzhou Liu, Santa Clara; Aubry Kern Miller, San Francisco; David George Putman, Saratoga; Klaus Kurt Weinhardt, Palo Alto; Shu-Hai Zhao, Sunnyvale, all of Calif.

[73] Assignee: Syntex (U.S.A.) Inc., Palo Alto, Calif.

[21] Appl. No.: 08/976,418

[22] Filed: Nov. 21, 1997

Related U.S. Application Data

[63] Continuation-in-part of application No. 08/963,390, Nov. 3, 1997, and a continuation-in-part of application No. 08/858,964, May 20, 1997, Pat. No. 5,863,924
[60] Provisional application No. 60/040,377, Mar. 10, 1997, and provisional application No. 60/018,218, May 23, 1996.

[51] Int. Cl.⁶ ..................... A61K 31/505; C07D 239/42
[52] U.S. Cl. ................ 514/272; 514/275; 544/321; 544/330; 544/331
[58] Field of Search .................... 514/272, 275; 544/321, 330, 331

[56] References Cited

U.S. PATENT DOCUMENTS

| | | | |
|---|---|---|---|
| 3,965,101 | 6/1976 | Yale et al. | 544/330 |
| 4,543,248 | 9/1985 | Stringfellow et al. | 514/272 |
| 4,619,933 | 10/1986 | Stringfellow et al. | 514/272 |
| 4,665,077 | 5/1987 | Stringfellow et al. | 514/269 |
| 5,002,951 | 3/1991 | Stringfellow et al. | 514/272 |
| 5,147,876 | 9/1992 | Mizuchi et al. | 514/275 |
| 5,223,505 | 6/1993 | Hargreaves et al. | 514/256 |
| 5,457,101 | 10/1995 | Greenwood et al. | 514/220 |
| 5,698,444 | 12/1997 | Baez et al. | 435/325 |
| 5,705,519 | 1/1998 | Audia et al. | 514/415 |
| 5,736,544 | 4/1998 | Audia et al. | 514/247 |

FOREIGN PATENT DOCUMENTS

| | | |
|---|---|---|
| 0114770 | 8/1984 | European Pat. Off. . |
| 0210044 | 1/1987 | European Pat. Off. . |
| 0459830 | 12/1991 | European Pat. Off. . |
| 0521471 | 1/1993 | European Pat. Off. . |
| 1921049 | 11/1969 | Germany . |
| 2255525 | 5/1974 | Germany . |
| 2750288 | 5/1979 | Germany . |
| 3029871 | 2/1981 | Germany . |
| 4237768 | 5/1993 | Germany . |
| WO 85/00603 | 2/1985 | WIPO . |
| WO 85/00604 | 2/1985 | WIPO . |
| WO 86/04583 | 8/1986 | WIPO . |
| WO 89/07599 | 8/1989 | WIPO . |
| WO 89/11279 | 11/1989 | WIPO . |
| WO 96/32384 | 10/1996 | WIPO . |
| WO 96/39400 | 12/1996 | WIPO . |

OTHER PUBLICATIONS

D. Hoyer, et al., *Pharmacological Reviews*, (1994) vol. 46(2), pp. 157–203, "VII. International Union of Pharmacology Classification of Receptors for 5–Hydroxytryptamine."

(List continued on next page.)

*Primary Examiner*—Yogendra N. Gupta
*Attorney, Agent, or Firm*—Janet Pauline Clark; Janet K. Kaku

[57] ABSTRACT

The aryl pyrimidine derivatives and pharmaceutically acceptable salts and N-oxides thereof, exhibit useful pharmacological properties, including utility as selective $5HT_{2B}$-antagonists. The $5\text{-}HT_{2B}$ antagonist is a compound of the formula:

(I)

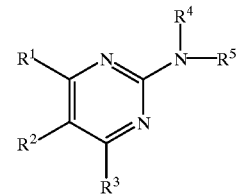

wherein:
  $R^1$ is hydrogen, alkyl, lower alkoxy, hydroxyalkyl, cycloalkyl, cycloalkyl lower alkyl, alkenyl, lower thioalkoxy, halo, fluoroalkyl, $-NR^6R^7$, $-CO_2R^8$, $-O(CH_2)_nR^9$, or lower alkyl optionally substituted with hydroxy, alkoxy, halo, or aryl; in which
    n is 1, 2, or 3;
    $R^6$ and $R^7$ are hydrogen or lower alkyl;
    $R^8$ is hydrogen or lower alkyl; and
    $R^9$ is hydrogen, lower alkyl, hydroxy, hydroxy lower alkyl, lower alkenyl, or lower alkoxy;
  $R^2$ is hydrogen, lower alkyl, lower alkoxy, halo, or lower fluoroalkyl;
  $R^3$ is optionally substituted aryl other than pyridyl, thienyl, or furanyl;
  $R^4$ is hydrogen, lower alkyl, cycloalkyl, alkenyl, acyl, amino, amido, aryl, $-(CH_2)_mNR^{10}R^{11}$, or lower alkyl optionally substituted by amino, monosubstituted amino, disubstituted amino, hydroxy, carboxy, aryl, lower alkoxy, amido, alkoxy carbonyl, tetrahydrofuran-2-yl, hydroxyalkoxy, or sulfonamido;
  in which
    $R^{10}$ and $R^{11}$ are hydrogen or lower alkyl; and
  $R^5$ is hydrogen or lower alkyl; provided that:
    (i) when $R^3$ is naphthyl, indol-1-yl, or 2,3-dihydroindol-1-yl, and $R^2$, $R^4$ and $R^5$ are all hydrogen, $R^1$ is not methyl;
    (ii) when $R^3$ is phenyl or naphthyl, $R^1$ is not $-NR^6R^7$;
    (iii) when $R^3$ is phenyl, $R^2$ is not lower alkoxy, and $R^1$ and $R^2$ are not halo;
    (iv) when $R^3$ is phenyl and $R^1$ is H, $R^2$ is not methyl; and
    (v) when $R^3$ is 1,2,3,4-tetrahydroquinolinyl, $R^4$ and $R^5$ are hydrogen;
or a pharmaceutically acceptable salt or N-oxide thereof.

7 Claims, No Drawings

OTHER PUBLICATIONS

G. Martin, et al., *Neuropharmacology,* (1994) vol. 33(3/4), pp. 261–173, "Classification Review. Receptors for 5–Hydroxytryptamine: Current Perspectives on Classification and Nomenclature."

Mokrosz, J.L., et al., *Pharmazie* (1994) vol. 49, No. 11, pp. 801–806, "Structure–activity relationship studies of CNS agents. Part 14: Structural requirementfor the 5–HT1A and 5–HT2A receptor selectivity of simple 1–(2–pyrimidinyl) piperazine derivatives".

Budesinsky et al., *Collection Czechoslav. Chem Commun.* (1961), vol. 26, pp. 2865–2870, "Über Die Darstellung Von–2–Sulfanilamido–4–Methylpyrimidinen Mit Einem Heterocyclischen Substituenten in 6–Stellung".

Mariella et al., *J. Org. Chem.* (1960), vol. 25, pp. 647–648, "Preparation of Various Substituted Pyrimidines".

Zagulyaeva et al., *Izv. Sib. Otd. Akad. Nauk SSSR, Ser. Khim. Nauk* (1990), vol. 4, pp. 27–31, "Synthesis of Methoxyalkyl Substituted 2–Aminopyrimidines From .Gamma.–Methoxyalkynyl Ketones".

Essawy et al., *Egypt. J. Chem.* (1994), vol. 37, No. 4, pp. 423–431, "Synthesis and Reactions of 2–Amino–4–Aryl–6–(2'–Methoxynaphthyl)Pyrimidines".

Richardson, B.P., *Ann. N.Y. Acad. Sci* (1990), vol. 600, pp. 511–520, "Serotonin and Pain".

ARYL PYRIMIDINE DERIVATIVES AND USES THEREOF

CROSS-REFERENCE TO RELATED APPLICATIONS

This application is a CIP of U.S. application Ser. No. 08/963,390 filed Nov. 3, 1997 entitled "Aryl Pyrimidine Derivatives" by Jacob Berger, Lee Allen Flippin, Robert Greenhouse, Saul Jaime-Figueroa, Yanzhou Liu, Aubry Kern Miller, David George Putman, Klaus Kurt Weinhardt and Shu-Hai Zhao (Attorney Docket No. R0015D-CIP) and a CIP of U.S. Application No. 08/858,964, filed May 20, 1997, now U.S. Pat. No. 5,863,924, which claims benefit under 35 U.S.C. 119(e) of U.S. Provisional Application Nos. 60/040,377, filed Mar. 10, 1997, and 60/018,218, filed May 23, 1996.

FIELD OF THE INVENTION

The present invention relates to methods of use for aryl pyrimidine derivatives and pharmaceutically acceptable salts and N-oxides thereof, which exhibit useful pharmacological properties, including utility as selective $5HT_{2B}$-antagonists.

BACKGROUND INFORMATION AND RELATED DISCLOSURES

Serotonin, a neurotransmitter with mixed and complex pharmacological characteristics, was first discovered in 1948, and subsequently has been the subject of substantial research. Serotonin, also referred to as 5-hydroxytryptamine (5-HT), acts both centrally and peripherally on discrete 5-HT receptors. Currently, fourteen subtypes of serotonin receptor are recognized and delineated into seven families, $5-HT_1$, to $5-HT_7$. Within the $5-HT_2$ family, $5-HT_{2A}$, $5-HT_{2B}$, and $5-HT_{2C}$ subtypes are known to exist. These subtypes share sequence homology and display similarities in their specificity for a wide range of ligands. Nomenclature and classification of 5-HT receptors have been reviewed recently (see Martin and Humphrey, *Neuropharm.* 1994, 33, 261–273 and Hoyer et al., *Pharm. Rev.* 1994, 46, 157–203).

The $5-HT_{2B}$ receptor, initially termed $5-HT_{2F}$, or serotonin-like receptor, was first characterized in rat isolated stomach fundus (see Clineschmidt et al., *J. Pharmacol. Exp. Ther.* 1985, 235, 696–708; Cohen and Wittenauer, *J. Cardiovasc. Pharmacol.* 1987, 10, 176–181). The $5-HT_{2C}$ receptor, widely distributed in the human brain, was first characterized as a $5-HT_{1C}$ subtype (see Pazos et al., *Eur. J. Pharmacol.* 1984, 106, 539–546) and was subsequently recognized as belonging to the $5-HT_2$ receptor family (see Pritchett et al., *EMBO J.* 1988, 7, 4135–4.140).

Because of the similarities in the pharmacology of ligand interactions at $5-HT_{2B}$ and $5-HT_{2C}$ receptors, many of the therapeutic targets that have been proposed for $5-HT_{2C}$ receptor antagonists are also targets for $5-HT_{2B}$ receptor antagonists. Current evidence strongly supports a therapeutic role for $5-HT_{2B/2C}$ receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism. Additionally, current evidence strongly supports a therapeutic role for selective $5-HT_{2B}$ receptor antagonists that will offer distinct therapeutic advantages collectively in efficacy, rapidity of onset and absence of side effects. Such agents are expected to be useful in the treatment of hypertension, disorders of the gastrointestinal track (e.g., irritable bowel syndrome, hypertonic lower esophageal sphincter, motility disorders), restenosis, asthma and obstructive airway disease, and prostatic hyperplasia (e.g., benign prostatic hyperplasia).

Numerous aryl substituted pyrimidine compounds have been exemplified in the chemical and patent literature. For example, Budesinsky et al., *Collection Czechoslav. Chem. Commun.* 1961, 26, 2865–2870, disclose 2-amino-6-methyl-4-(naphth-1-yl)-pyrimidine as an intermediate useful in the preparation of antibacterial compounds. Other pyrimidine derivatives are described in Mariella et al., *J. Org. Chem.* 1960, 25, 647–648; Zagulyaeva et al., *Izv. Sib. Otd. Akad. Nauk SSSR, Ser. Khim. Nauk* 1990, 4, 27–31; Essawy et al., *Egypt. J. Chem.* 1994, 37(4), 423–31; U.S. Pat. Nos. 4,543, 248, 4,619,933, 4,665,077, and 5,002,951, all to Stringfellow et al.; U.S. Pat. No. 5,147,876 to Mizuchi et al.; U.S. Pat. No. 5,223,505 to Hargreaves et al.; and European Patent Published Application EP 0 459 830, assigned to the Wellcome Foundation.

The disclosures of these and other documents referred to throughout this application are incorporated herein by reference.

SUMMARY OF THE INVENTION

The invention relates to a method for treating a mammal having a disease state which is alleviable by treatment with a $5HT_{2B}$ antagonist, by administering to a mammal in need thereof a therapeutically effective amount of a compound of Formula I:

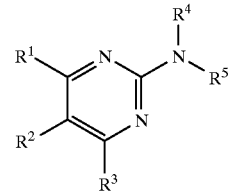

wherein:

$R^1$ is hydrogen, alkyl, lower alkoxy, hydroxyalkyl, cycloalkyl, cycloalkyl lower alkyl, alkenyl, lower thioalkoxy, halo, fluoroalkyl, optionally substituted phenyl, $-NR^6R^7$, $-CO_2R^8$, $-O(CH_2)_nR^9$, or lower alkyl optionally substituted with hydroxy, lower alkoxy, halo, or aryl;

in which n is 1, 2, or 3;

$R^6$ and $R^7$ are independently hydrogen or lower alkyl;

$R^8$ is hydrogen or lower alkyl; and $R^9$ is hydrogen, lower alkyl, hydroxy, hydroxy lower alkyl, lower alkenyl, or lower alkoxy;

$R^2$ is hydrogen, lower alkyl, lower alkoxy, halo, or lower fluoroalkyl;

$R^3$ is optionally substituted aryl;

$R^4$ is hydrogen, lower alkyl, cycloalkyl, alkenyl, acyl, amino, amido, aryl, $-C(NH)NR^{10}R^{11}$, $-SO_2R^{12}$, or lower alkyl optionally substituted with amino, mono-substituted amino, disubstituted amino, hydroxy, carboxy, aryl, lower alkoxy, amido, alkoxycarbonyl, tetrahydrofuran-2-yl, hydroxyalkoxy, or sulfonamido;

in which $R^{10}$ and $R^{11}$ are independently hydrogen or lower alkyl, and $R^{12}$ is lower alkyl; and $R^5$ is hydrogen or lower alkyl;
or a pharmaceutically acceptable salt or N-oxide thereof.

DETAILED DESCRIPTION OF THE INVENTION

Definitions

As used herein:

"Alkyl" means a branched or unbranched saturated hydrocarbon chain containing 1 to 12 carbon atoms, such as methyl, ethyl, propyl, tert-butyl, n-hexyl, n-octyl, n-dodecyl, and the like.

"Alkenyl" refers to an unsaturated monovalent hydrocarbon radical of 1 to 12 carbon atoms. This term is further exemplified by such radicals as vinyl, prop-2-enyl, pent-3-enyl, hex-5-enyl, oct-2-enyl, and the like.

"Cycloalkyl" means a monovalent saturated carbocyclic radical containing no unsaturation and having from three to eight carbon atoms, e.g., cyclopropyl, 2-methylcyclopropyl, cyclobutyl, 3-ethylcyclobutyl, cyclopentyl, cyclohexyl, cycloheptyl, cyclooctyl.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkenyl" refers to an unsaturated monovalent hydrocarbon radical of one to six carbon atoms. This term is further exemplified by such radicals as vinyl, prop-2-enyl, pent-3-enyl, and hex-5-enyl.

"Cycloalkyl lower alkyl" as defined herein means cycloalkyl as defined above attached to a lower alkyl radical as defined above, for example e.g., cyclopropylmethyl, cyclopropylethyl, cyclopropylpropyl, cyclobutylmethyl, cyclobutylethyl, cyclopentylmethyl, cyclohexylmethyl, cycloheptylmethyl, cyclooctylmethyl, and the like.

"Phenyl lower alkyl" means phenyl attached to a lower alkyl radical as defined above, for example phenylmethyl (benzyl), phenethyl, phenylpropyl, and the like.

"Fluoroalkyl" means alkyl as defined above substituted by 1 to 5 fluorine atoms in any position, for example trifluoromethyl, pentafluoroethyl, 1,1,1-trifluoro-n-propyl, 1-fluoro-n-butyl, 1,2-difluoro-3-methylpentane, 1-fluorooctane, and the like.

"Lower fluoroalkyl" means lower alkyl as defined above substituted by 1 to 5 fluorine atoms in any position, for example trifluoromethyl, pentafluoroethyl, 1,1,1-trifluoro-n-propyl, 1-fluoro-n-butyl, 1,2-difluoro-3-methylpentane, and the like.

"Acyl" refers to the group —C(O)—R', where R' is lower alkyl as herein defined.

"Lower alkoxy" means the group —O—R' wherein R' is lower alkyl as herein defined. Likewise, "lower thioalkoxy" denotes the group —S—R'.

"Hydroxyalkyl" means the group alkyl as defined above substituted by 1, 2 or 3 hydroxy groups, for example hydroxymethyl, 1-hydroxyethyl, 2-hydroxyethyl, 1,2-dihydroxyethyl, 1-hydroxyisopropyl, 2-hydroxyisopropyl, 1,2-dihydroxyisopropyl, 1-hydroxybutyl, 1,3-dihydroxybutyl, and the like. Similarly, "hydroxy lower alkyl" means the group lower alkyl as defined above substituted by 1, 2 or 3 hydroxy groups.

"Halo" denotes fluoro, chloro, bromo, or iodo, unless otherwise indicated.

"Monosubstituted amino" means a radical —NHR where R is lower alkyl or optionally substituted lower alkyl as herein defined, for example, methylamino, ethylamino, or the like.

"Disubstituted amino" means a radical —NR$^a$R$^b$, where R$^a$ and R$^b$ are independently selected from lower alkyl or optionally substituted lower alkyl as herein defined, for example dimethylamino, diethylamino.

"Alkoxycarbonyl" means a radical —C(O)OR$^c$ where R$^c$ is lower alkyl or aryl as herein defined, for example methoxycarbonyl or phenoxycarbonyl.

"Amido" means a radical =13 C(O)NR$^d$R$^e$ where R$^d$ and R$^e$ are independently hydrogen, lower alkyl, or aryl as herein defined.

"Sulfonamido" means a radical —NR$^f$SO$^2$R$^g$ where R$^f$ and R$^g$ are independently hydrogen or lower alkyl as herein defined, for example methanesulfonamido.

"Hydroxyalkoxy" means lower alkoxy as herein defined substituted with a hydroxy group, for example 2-hydroxyethoxy.

"Optional" or "optionally" means that the subsequently described event or circumstance may or may not occur, and that the description includes instances where said event or circumstance occurs and instances in which it does not. For example, "optionally substituted phenyl" or "optionally substituted aryl" means that phenyl or aryl may or may not be substituted with a substituent selected from the group consisting of lower alkyl, lower alkoxy, hydroxy, nitro, lower fluoroalkyl, and halo, and encompasses unsubstituted phenyl and unsubstituted aryl and all possible isomeric phenyl and aryl radicals that are mono, di or trisubstituted. Similarly, "lower alkyl optionally substituted by" means that lower alkyl may or may not be substituted with a substituent selected from the group consisting of amino, monosubstituted amino, disubstituted amino, hydroxy, carboxy, aryl, lower alkoxy, amido, alkoxycarbonyl, tetrahydrofuran-2-yl, hydroxyalkoxy, or sulfonamido, and their isomeric forms.

The term "aryl" as used herein means a monocyclic aromatic ring, or a 9 to 14 membered bicyclic or tricyclic ring system in which at least one ring is aromatic in nature, and includes carbocycles, and heterocycles having one or two heteroatoms chosen from nitrogen, oxygen, and sulfur. Examples of aryl groups include, but are not limited to, phenyl, thiophene, naphthalene, acenaphthene, anthracene, phenanthrene, quinoline, isoquinoline, 1,2,3,4-tetrahydroquinoline, indole, 2,3-dihydroindole, 1H-benzo[b]azepine, 2,3,4,5-tetrahydro-1H-benzo[b]azepine, 2H-benzo[1,4]oxazine, 3,4-dihydro-2H-benzo[1,4]oxazine, 1H,3H-benzo[de]isochromene, 6,7,8,9-tetrahydro-5-oxa-9-benzocycloheptane, 2,3-dihydro-1,4-benzodioxane, and the like. More specifically, the term aryl includes structures of the formula:

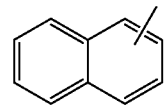

e.g., naphth-1-yl and naphth-2-yl, and derivatives thereof;

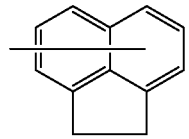

e.g., acenaphthen-5-yl and acenaphthen-6-yl, and derivatives thereof;

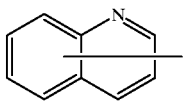

e.g., quinolin-2-yl, quinolin-4-yl, quinolin-8-yl, and the like, and derivatives thereof;

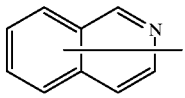

e.g., isoquinolin-1-yl, isoquinolin-4-yl, isoquinolin-8-yl, and the like, and derivatives thereof;

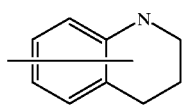

e.g., 1,2,3,4-tetrahydroquinolin-1-yl, 1,2,3,4-tetrahydroquinolin-5-yl, and derivatives thereof;

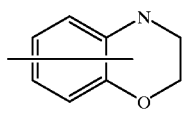

e.g., 3,4-dihydro-2H-benzo[1,4]oxazin-1-yl, 3,4-dihydro-2H-benzo[1,4]oxazin-5-yl, and derivatives thereof;

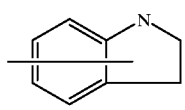

where the dotted line represents an optional double bond, e.g., indol-1-yl, 1H-indol-4-yl, 2,3-dihydroindol-1-yl, and derivatives thereof;

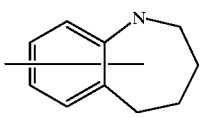

e.g., 2,3,4,5-tetrahydro-1H-benzo[b]azepine, and derivatives thereof;

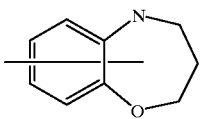

e.g., 7,8,-dihydro-6H-5-oxa-9-aza-benzocyclohepten-9-yl, 7,8,-dihydro-6H-5-oxa-9-aza-benzocyclohepten-4-yl, and derivatives thereof;

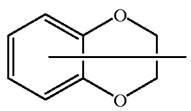

e.g., benzo-1,4-dioxane, and derivatives thereof.

The terms "inert organic solvent" or "inert solvent" mean a solvent inert under the conditions of the reaction being described in conjunction therewith [including, for example, benzene, toluene, acetonitrile, tetrahydrofuran, dimethylformamide, chloroform ($CHCl_3$), methylene chloride (or dichloromethane or $CH_2Cl_2$), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"N-oxide" refers to the stable amine oxide formed at one of the pyrimidine nitrogen atoms.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "therapeutically effective amount" refers to that amount of a compound of Formula I that is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

The term "disease state which is alleviable by treatment with a $5HT_{2B}$ antagonist" as used herein is intended to cover all disease states which are generally acknowledged in the art to be usefully treated with compounds having affinity for $5HT_{2B}$ receptors in general, and those disease states which have been found to be usefully treated by the specific compounds of our invention, the compounds of Formula I. Such disease states include, but are not limited to, anxiety (e.g., generalized anxiety disorder, panic disorder and obsessive compulsive disorder), alcoholism and addiction to other drugs of abuse, depression, migraine, hypertension, disorders of the gastrointestinal track (e.g., irritable bowel syndrome, hypertonic lower esophageal sphinter, motility disorders), restenosis, asthma and obstructive airway disease, prostatic hyperplasia (e.g., benign prostatic hyperplasia), sleep disorders, feeding disorders (e.g., anorexia nervosa), and priapism.

Nomenclature

The compounds of Formula I, illustrated below, will be named using the indicated numbering system:

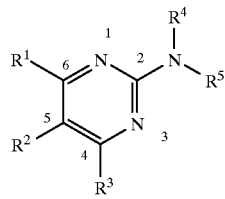

A compound of Formula I wherein $R^1$ is isopropyl, $R^2$, $R^4$ and $R^5$ are hydrogen, and $R^3$ is 1-naphthyl, is named: 2-amino-6-isopropyl-4-(naphth-1-yl)-pyrimidine.

A compound of Formula I wherein $R^1$ is tert-butyl, $R^2$, $R^4$ and $R^5$ are hydrogen, and $R^3$ is 5-acenaphthen, is named: 4-(acenaphthen-5-yl)-2-amino-6-tert-butylpyrimidine.

A compound of Formula I wherein $R^1$ is isopropyl, $R^2$, $R^4$ and $R^5$ are hydrogen, and $R^3$ is 1H-indol-4-yl, is named: 2-amino-4-(1H-indol-4-yl)-6-isopropylpyrimidine.

A compound of Formula I wherein $R^1$ is methyl, $R^2$ and $R^4$ are hydrogen, $R^5$ is methyl, and $R^3$ is 1,2,3,4-tetrahydroquinolin-1-yl, is named: 4-(3,4-dihydro-2H-quinolin-1-yl)-2-(methylamino)-6-methylpyrimidine.

A 1-N-oxide of a compound of Formula I wherein $R^1$ is chloro, $R^2$ is methyl, $R^4$ and $R^5$ are hydrogen, and $R^3$ is 4-methoxyphenyl, is named: 2-amino-6-chloro-4-(4-methoxyphenyl)-5-methylpyrimidine-1-N-oxide.

Preferred Embodiments

Among the family of compounds of the present invention, one preferred category includes the compounds of Formula I in which $R^4$ and $R^5$ are both hydrogen. Within this category a preferred group includes the compounds where $R^1$ is lower alkyl and $R^3$ is optionally substituted aryl, especially where $R^3$ is optionally substituted 1-naphthyl, 5-acenaphthen, or indol-4-yl, and N-oxides thereof.

At present, the preferred compounds are:

2-amino-4-(2-methylnaphth-1-yl)-6-methylpyrimidine;
2-amino-4-(4-fluoronaphth-1-yl)-6-isopropylpyrimidine
2-amino-4-(4-fluoronaphth-1-yl)-6-isopropylpyrimidine-1-N-oxide;
2-amino-4-(4-fluoronaphth-1-yl)-6-(2-methylpropyl)-pyrimidine;
2-amino-6-(tert-butyl)-4-(4-fluoronaphth-1-yl)-pyrimidine;
2-amino-4-(1H-indol-4-yl)-6-methylpyrimidine;
2-amino-4-(4-fluoronaphth-1-yl)-6-(1-fluoro-1-methylethyl)-pyrimidine;
2-amino-4-(4-fluoronaphth-1-yl)-6-(1-hydroxy-1-methylethyl)-pyrimidine;
4-(acenaphthen-5-yl)-2-amino-6-isopropylpyrimidine; and
4-(acenaphthen-5-yl)-2-amino-6-tert-butylpyrimidine.

METHODS OF PREPARATION

Preparation of Compounds of Formula I

One method of preparation of compounds of Formula I is from intermediates of formula (4), the preparation of which is shown in Reaction Scheme I below.

REACTION SCHEME I

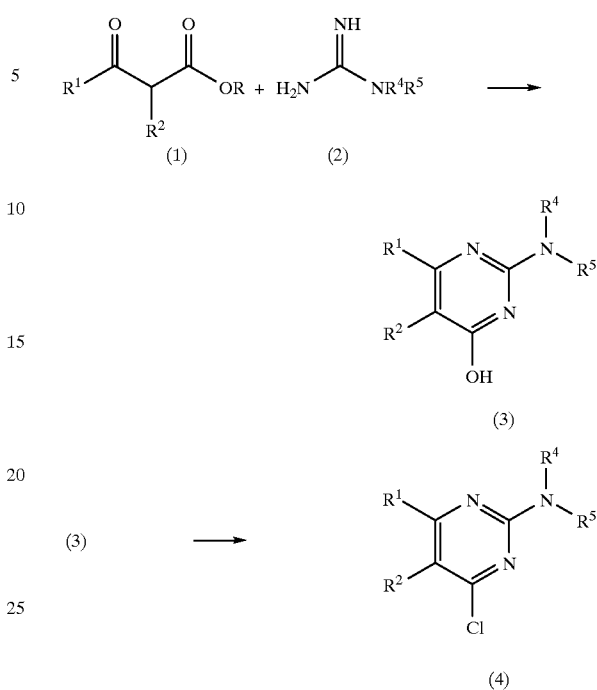

where R is lower alkyl, and $R^1$ and $R^2$ are as defined in the Summary of the Invention, and $R^4$ and $R^5$ are hydrogen or lower alkyl.

Preparation of Compounds of Formula (3)

The starting ketoester of formula (1) may be obtained commercially, for example from Aldrich Chemical Co., Inc., or may be prepared according to methods well known in the art. The guanidine or substituted guanidine compounds of formula (2) are commercially available, or may be prepared according to methods well known in the art.

To prepare compounds of formula (3), a ketoester of formula (1) is treated with an excess of a guanidine derivative of formula (2) in a protic solvent, preferably ethanol, at reflux temperature for about 6–24 hours, preferably about 16 hours. The product of formula (3), a 2-amino-4-hydroxypyrimidine derivative, is isolated by conventional means, and preferably reacted in the next step with no further purification.

Preparation of Compounds of Formula (4)

The 2-amino-4-hydroxypyrimidine derivative of formula (3) is converted to the corresponding 4-chloro compound of formula (4) by reacting a compound of formula (3) with a chlorinating agent, preferably phosphorous oxychloride, preferably in the absence of solvent. The reaction is conducted at reflux temperature for about 30 minutes to 8 hours, preferably about 2 hours. The product of formula (4), a 2-amino-4-chloropyrimidine derivative, is isolated by conventional means, and is preferably recrystallized before further reaction.

Alternatively, the 2-amino-4,6-dichloro compound of formula (4) may be converted to the corresponding 6-alkoxy-4-chloro compound of formula (4) by reacting the 4,6-dichloro compound of formula (4) with the corresponding alcohol in the presence of base, preferably potassium hydroxide or potassium tert-butoxide. The reaction is conducted at a temperature of about 10° to 100° C. for about 5 minutes to 10 hours. The product of formula (4), a 6-alkoxy-4-chloropyrimidine derivative, is isolated by conventional means, and purified by chromatography.

Preparation of Compounds of Formula I

One method of converting a compound of formula (4) to a compound of Formula I is shown below in Reaction Scheme II.

REACTION SCHEME II

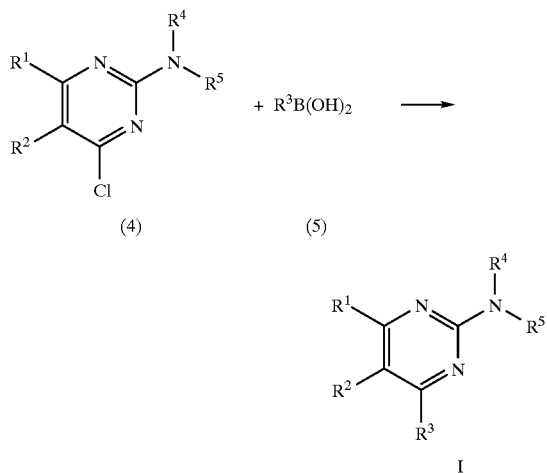

where $R^1$, $R^2$ and $R^3$ are as defined in the Summary of the Invention, and $R^4$ and $R^5$ are hydrogen or lower alkyl.

Preparation of Compounds of Formula I

A 2-amino-4-chloropyrimidine derivative of formula (4) is reacted with a boronic acid derivative of formula (5) in an aqueous solvent, preferably a mixture of ethanol, water and dimethoxyethane, containing a palladium catalyst, preferably palladium tetrakistriphenylphosphine, and an inorganic base, preferably sodium carbonate. The reaction is preferably carried out at the reflux temperature of the solvent, preferably about 80–90° C., for about 5–30 hours, preferably about 14 hours. The product of Formula I is isolated by conventional means, and preferably purified by recrystallization.

Alternative Preparation of Compounds of Formula I

An alternative method of converting a compound of formula (4) to a compound of Formula I is shown below in Reaction Scheme III.

REACTION SCHEME III

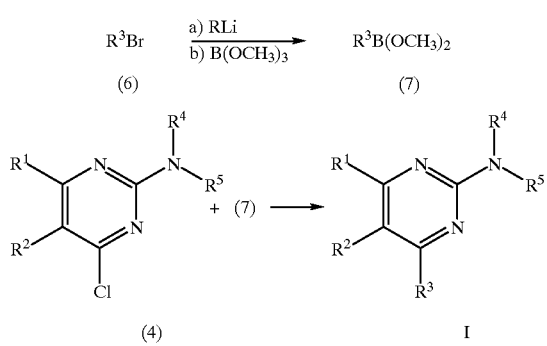

where R is lower alkyl, $R^1$, $R^2$ and $R^3$ are as defined in the Summary of the Invention, and $R^4$ and $R^5$ are hydrogen or lower alkyl.

Preparation of Compounds of Formula (7)

The bromoaryl derivative of formula (6) is reacted with a strong base, for example a lower alkyl lithium, preferably n-butyl lithium. The reaction is carried out in an ethereal solvent (for example, diethyl ether, dimethoxyethane, dioxane or tetrahydrofuran, preferably tetrahydrofuran), at a temperature of about −50 to −150° C., preferably about −95° C., for about 5–30 minutes, after which time about 1 equivalent of a trialkoxyborane, preferably trimethoxyborane, is added, and the mixture allowed to warm to room temperature. The product of formula (7), a dimethoxyborane complex, is isolated by removal of solvent, and used in the next reaction with no further purification.

Preparation of Compounds of Formula I

A 2-amino-4-chloropyrimidine derivative of formula (4) is reacted with the boron complex of formula (7) obtained above in an inert solvent, preferably an aromatic solvent, most preferably toluene, containing a palladium catalyst, preferably palladium tetrakistriphenylphosphine, and an aqueous inorganic base, preferably sodium carbonate/water. The reaction is preferably carried out at the reflux temperature of the solvent, preferably about 80–90° C., for about 10 minutes to 10 hours, preferably about 1 hour. The product of Formula I is isolated and purified by conventional means, preferably purified by chromatography.

Preparation of Compounds of Formula I where $R^3$ is a Bicyclic Ring System containing N as the Point of Attachment An alternative method is available for converting a compound of formula (4) to a compound of Formula I, in which $R^3$ is a bicyclic ring system containing N as the point of attachment to the pyrimidine nucleus, i.e., $R^3$ is represented as:

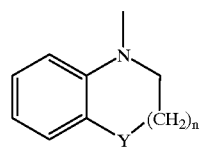

in which n is 0, 1 or 2, Y is $CH_2$, O, S or NH, and the rings are optionally substituted as defined above. This method is shown below in Reaction Scheme IV.

REACTION SCHEME IV

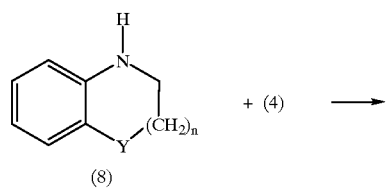

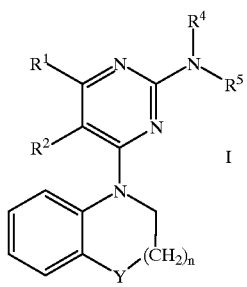

in which n is 0, 1 or 2, Y is $CH_2$, O, S or NH, and $R^1$, $R^2$, $R^4$ and $R^5$ are as defined above in the Summary of the Invention.

Preparation of Compounds of Formula I

A 2-amino-4-chloropyrimidine derivative of formula (4) is reacted with the compound of formula (8) in a mixture of water and a strong acid, preferably sulfuric acid, as a solvent. The reaction is preferably carried out at a temperature of about 100° C., for about 20 minutes to 10 hours, preferably about 2 hours. The product of Formula I is isolated by conventional means, and preferably purified by recrystallization.

Alternatively, the compounds of formula (4) and (8) are reacted together in a polar solvent, preferably dimethylformamide. The reaction is preferably carried out at a temperature of about 70–90° C., for about 12–72 hours, preferably about 24 hours. The product of Formula I is isolated by conventional means, and preferably purified by chromatography.

Preparation of Compounds of Formula I from Acyl Derivatives

Compounds of Formula I can also be prepared starting from acyl aryl derivatives of formula (9), as shown below in Reaction Scheme V.

REACTION SCHEME V

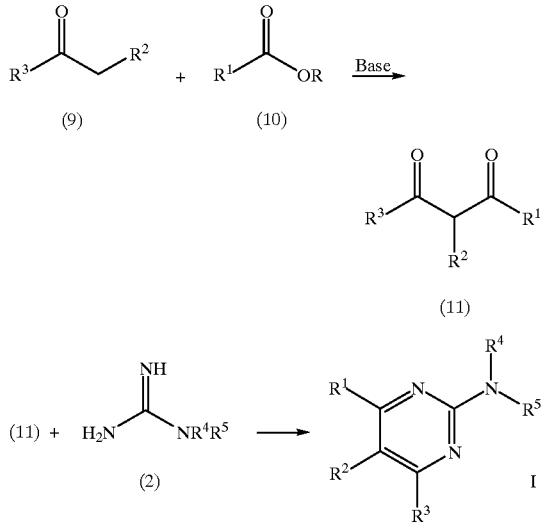

where R is lower alkyl, $R^4$ and $R^5$ are independently hydrogen or lower alkyl, and $R^1$, $R^2$ and $R^3$ are as defined in the Summary of the Invention.

Preparation of Compounds of Formula (9)

An acyl aryl derivative of formula (9) may be obtained commercially, for example from Aldrich Chemical Co., Inc., or may be prepared according to methods well known in the art, for example, Friedel-Crafts reaction. In general, an aryl derivative of formula R H is reacted with an acylating agent, preferably acetic anhydride in the presence of Lewis acid, for example aluminum chloride. The reaction is carried out at a temperature of about −20° to 20° C., preferably 0° C. for about 5 minutes to 3 hours, preferably 20 minutes. The product of formula (9), an acyl aryl derivative, is isolated by conventional means, and preferably purified by chromatography.

Preparation of Compounds of Formula (11)

An acyl aryl derivative of formula (9) is reacted with a large excess of an ester of formula (10) in the presence of a strong base, preferably sodium hydride. The reaction is preferably carried out at a temperature of about 80° C., until the compound of formula (9) is consumed. The dione of formula (11) is isolated by conventional means, and preferably purified by chromatography.

Preparation of Compounds of Formula I

The dione of formula (11) is reacted with the compound of formula (2), preferably in the absence of solvent. The reaction is carried out at a temperature of about 100–180° C., preferably at about 150° C., for about 1–10 hours, preferably about 5 hours. The product of Formula I is isolated by conventional means, and preferably purified by chromatography.

Alternative Preparation of Compounds of Formula I where $R^1$ is Hydrogen from a Compound of Formula (9)

An alternative method of preparation of compounds of Formula I where $R^1$ is hydrogen from acyl aryl derivatives of formula (9) is shown below in Reaction Scheme VI.

REACTION SCHEME VI

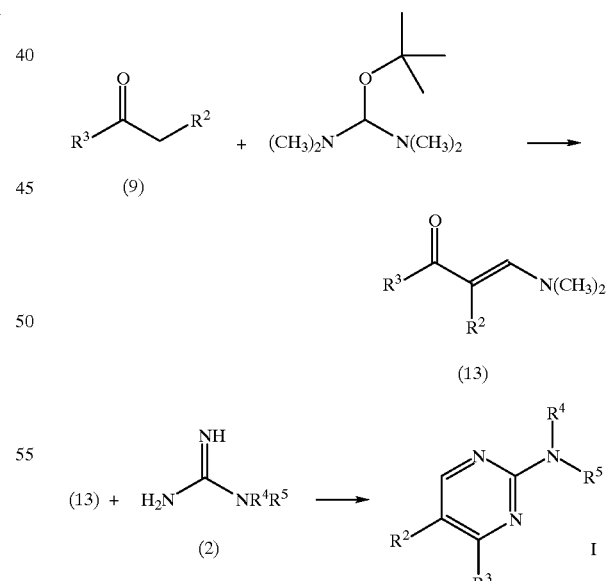

where $R^4$ and $R^5$ are independently hydrogen or lower alkyl, and $R^2$ and $R^3$ are as defined in the Summary of the Invention.

Preparation of Compounds of Formula (13)

An acyl aryl derivative of formula (9) is reacted with tert-butoxybis(dimethylamino)methane (Bredereck's reagent) in a protic solvent, preferably ethanol. The reaction is preferably carried out at a temperature of about 80° C., for about 12 hours to 5 days, preferably about 2 days. The compound of formula (13) is isolated by conventional means, and preferably used in the next reaction with no further purification.

Preparation of Compounds of Formula I

The enone of formula (13) is reacted with the compound of formula (2), preferably in the absence of solvent. The reaction is carried out at a temperature of about 100–180° C., preferably at about 120° C., for about 5–24 hours, preferably about 14 hours. The product of Formula I is isolated by conventional means, and preferably purified by recrystallization.

Alternative Preparation of Compounds of Formula I from Thio Derivatives

An alternative method of preparation of compounds of Formula I is from thio intermediates of formula (16) is shown below in Reaction Scheme VII.

REACTION SCHEME VII

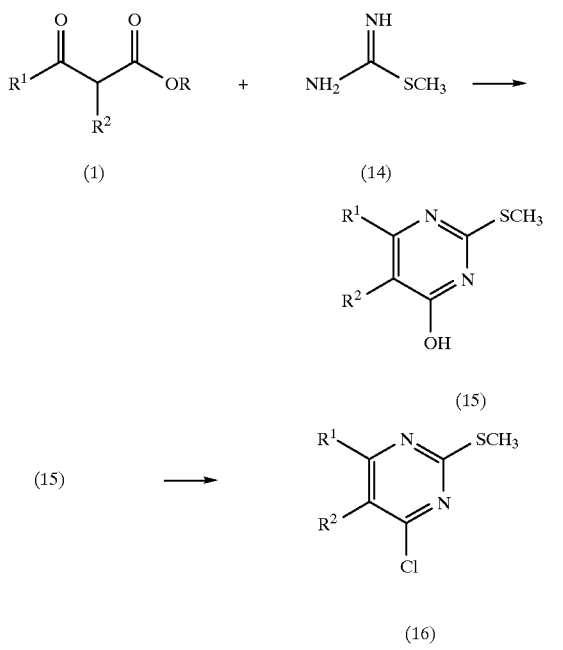

where R is lower alkyl, and $R^1$, and $R^2$ are as defined in the Summary of the Invention.

Preparation of Compounds of Formula (15)

The starting ketoester of formula (1) may be obtained commercialy, for example from Aldrich Chemical Co., Inc., or may be prepared according to methods well known in the art. The compounds of formula (14) are commercially available or may be prepared according to methods well known in the art.

A ketoester of formula (1) is treated with about 2 molar equivalents of an isothiourea derivative of formula (14) in an aqueous solution containing an excess of an inorganic base, preferably sodium carbonate. The reaction is carried out at a temperature range from about 5° C. to 60° C., preferably at about 25° C., for about 10 to 100 hours, preferably 60 hours. The product of formula (15), 4-hydroxy-2-methylthiopyrimidine derivative, is isolated by conventional means and preferably reacted in the next step with no further purification.

Preparation of Compounds of Formula (16)

The 4-hydroxy-2-methylthiopyrimidine derivative of formula (15) is converted to the corresponding 4-chloro compound of formula (16) under conditions similar to that shown above for the preparation of compounds of formula (4) in Reaction Scheme I. The product of formula (16), 4-chloro-2-methylthiopyrimidine derivative, is isolated by conventional means.

Preparation of Compounds of Formula I

One method of converting a compound of formula (16) to a compound of Formula I is shown below in Reaction Scheme VIII.

REACTION SCHEME VIII

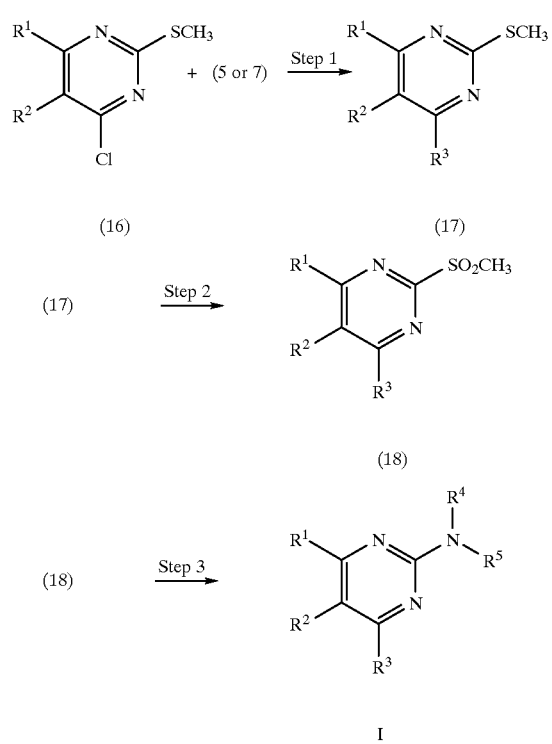

where $R^1$, $R^2$ and $R^3$ are as defined in the Summary of the Invention.

Step 1—Preparation of Compounds of Formula (17) where $R^1$ is Lower Alkyl

A 4-chloro-2-methylthiopyrimidine compound of formula (16) is reacted with a boronic acid derivative of formula (5) or a dimethoxyborane complex of formula (7), and following of the procedures of Reaction Schemes II or III, respectively, the product of formula (17), 2-methylthiopyrimidine derivative where $R^1$ is lower alkyl, is isolated and purified by conventional means.

Alternative Step 1—Preparation of Compounds of Formula (17) where $R^1$ is Lower Alkyl Substituted with Aryl or Hydroxy The 2-methylthiopyrimidine product of formula (17) where $R^1$ is lower alkyl that was obtained above may be converted to a 2-methylthiopyrimidine derivative of formula (17) where $R^1$ is lower alkyl substituted by aryl or hydroxy. The lower alkyl derivative of formula (17) is reacted with an excess of a hindered base, preferably lithium diisopropylamide, in an anhydrous ethereal solvent, preferably tetrahydrofuran at a temperature range of about −90° C. to 10° C., preferably at about −70° C., for about 30 minutes.

An excess of an alkylating agent, for example benzyl bromide or benzaldehyde, is added and the reaction mixture allowed to warm to ambient temperature. The product of formula (17) where $R^1$ is lower alkyl substituted by aryl or hydroxy, is then isolated and purified by conventional means, preferably by chromatography.

Step 2—Preparation of Compounds of Formula (18)

A 2-methylthiopyrimidine derivative of formula (17) is reacted with about 2–4 molar equivalents, preferably about 2 molar equivalents, of a strong oxidizing agent, for example meta-chloroperbenzoic acid. The reaction is carried out in an inert solvent, preferably methylene chloride, in a temperature range from about 0° C. to 50° C., preferably about 25° C., for about 1 to 30 hours, preferably about 16 hours. The product of formula (18), a 2-methanesulfonylpyrimidine derivative, is isolated by conventional means.

Step 3—Preparation of Compounds of Formula I

A 2-methanesulfonylpyrimidine derivative of formula (18) is reacted with an excess of a primary or secondary amine in a suitable protic solvent, for example ethanol, or neat. The reaction is carried out in a sonication bath at a temperature range of about 10° to 150° C., preferably 45° C., for about 1 to 40 hours. The product of Formula I is isolated and purified by conventional means.

Miscellaneous Preparations of Compounds of Formula I

Miscellaneous routes to compounds of Formula I are shown in Reaction Scheme IX:

REACTION SCHEME IX

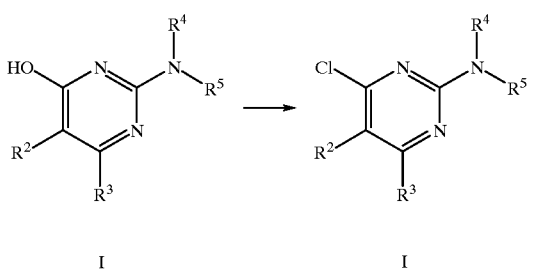

I
where $R^1$ is hydroxy

I
where $R^1$ is chloro

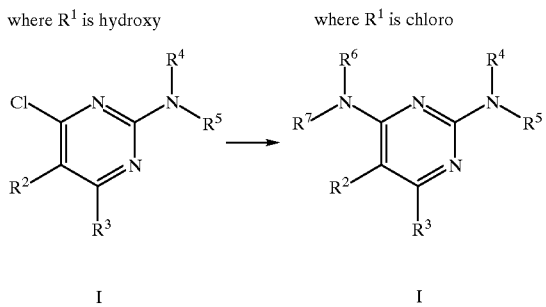

I
where $R^1$ is chloro

I
where $R^1$ is NR$^6$R$^7$

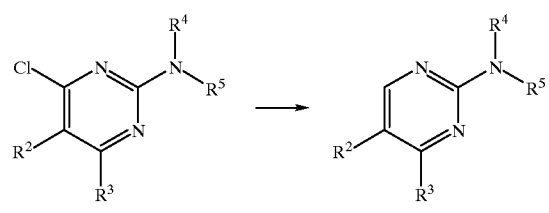

I
where $R^1$ is chloro

I
where $R^1$ is hydrogen where $R^4$ and $R^5$ are independently hydrogen or lower alkyl, and $R^2$ and $R^3$ are as defined in the Summary of the Invention.

Preparation of Compounds of Formula I where $R^1$ is Chloro

Compounds of Formula I where $R^1$ is chloro can be made from compounds of Formula I where $R^1$ is hydroxy in the same manner as shown in Reaction Scheme I, step 2, above.

Alternatively, compounds of Formula I where $R^1$ is chloro can be made from compounds of formula (4) where $R^1$ is chloro (i.e., 4,6-dichloro-pyrimidine derivatives) by reacting the dichloro derivative in the same manner as shown in Reaction Schemes II or III.

Preparation of Compounds of Formula I where $R^1$ is —NR$^6$R$^7$

A compound of Formula I where $R^1$ is chloro is reacted with a primary or secondary amine of formula R$^6$R$^7$NH, where R$^6$ is hydrogen or lower alkyl and R$^7$ is lower alkyl, in a high-boiling protic solvent, preferably ethylene glycol. The reaction is preferably carried out at a temperature of about 100° C., for about 12 hours to 5 days, preferably about 2 days. The compound of Formula I where $R^1$ is —NR$^6$R$^7$ is isolated by conventional means.

Preparation of Compounds of Formula I where $R^1$ is Hydrogen

A compound of Formula I where $R^1$ is chloro is catalytically reduced with hydrogen in the presence of a palladium or platinum catalyst, preferably palladium on carbon support. The reaction is carried out in a protic solvent, preferably methanol or ethanol, in the presence of a strong base, preferably aqueous sodium hydroxide. The reaction is preferably carried out at a temperature of about 10–40° C., preferably about room temperature, at about 1 atmosphere pressure until reduction is complete, about 1 hour. The compound of Formula I where $R^1$ is hydrogen is isolated by conventional means.

Preparation of Compounds of Formula I where $R^1$ is Thioalkoxy

The preparation of compounds of Formula I where $R^1$ is thioalkoxy is shown below in Reaction Scheme X.

REACTION SCHEME X

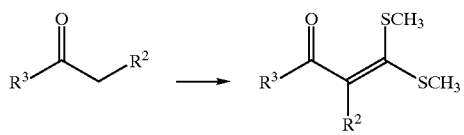

(9)                                      (19)

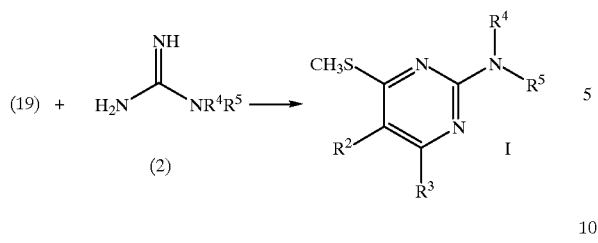

where $R^4$ and $R^5$ are independently hydrogen or lower alkyl, and $R^2$ and $R^3$ are as defined in the Summary of the Invention.

Preparation of Compounds of Formula (19)

An acyl aryl derivative of formula (9), which may be obtained commercially, for example from Aldrich Chemical Co., Inc., or may be prepared according to methods well known in the art, is mixed with carbon disulfide in an aprotic solvent, for example diethyl ether, benzene, toluene, preferably diethyl ether, in the presence of a strong base, preferably potassium tert-butoxide, at a temperature of about 10–12° C. The reaction mixture is allowed to warm to room temperature, then recooled to about 10–12° C., at which point 2 molar equivalents of methyl iodide is added dropwise. The mixture is maintained at a temperature of about 10–80° C., preferably about room temperature, for about 5–24 hours, preferably about 16 hours. The bis-methylsulfanyl compound of formula (19) is isolated by conventional means, and preferably purified by crystallization.

Preparation of I where $R^1$ is Thioalkoxy

The compound of formula (19) is reacted with the compound of formula (2) in the presence of a strong base, preferably sodium hydride, in an aprotic polar solvent, preferably dimethylformamide. The reaction is carried out at room temperature for about 1 hour, then at about 100–180° C., preferably at about 150° C., for about 1–10 hours, preferably about 5 hours. The product of Formula I is isolated by conventional means, and preferably purified by chromatography.

Preparation of I where $R^1$ is Alkoxy or Hydroxyalkoxy

The compound of formula (19) is reacted with the compound of formula (2) with the corresponding alcohol in an aprotic polar solvent, preferably dimethylformamide, in the presence of a strong base, preferably sodium hydride. The reaction is carried out at room temperature for about 1 hour, then at about 100–180° C., preferably at about 150° C., for about 1 to 10 hours, preferably about 5 hours. The product of Formula I is isolated by conventional means, and preferably purified by chromatography.

Preparation of N-Oxides of Compounds of Formula I

The preparation of N-oxides of compounds of Formula I is shown below in Reaction Scheme XI.

REACTION SCHEME XI

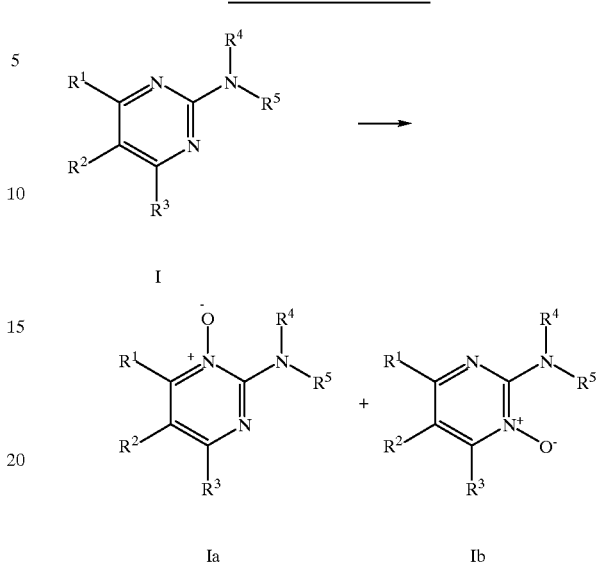

where $R^1$, $R^2$, $R^3$, $R^4$ and $R^5$ are as defined in the Summary of the Invention.

Preparation of N-Oxides of Formula I

A compound of Formula I is reacted with an oxidizing agent, preferably m-chloroperbenzoic acid, in an inert solvent, preferably chloroform or methylene dichloride. The reaction is preferably carried out at a temperature of about 30–60° C., preferably about 40° C., for about 10 minutes to 2 hours, preferably about 30 minutes. The N-oxide of the compound of Formula I is isolated by conventional means.

The position of the N-oxidation varies depending upon the steric hindrance of the $R^1$ group. For example, where $R^1$ is methyl, N-oxidation occurs almost exclusively at the 1-position (Formula Ia). However, as the $R^1$ group increases in size, increasing amounts of the 3-N-oxide (Formula Ib) are seen. For example, where $R^1$ is tert-butyl, most of the oxidation is directed toward the 3-position. For oxidations where a mixture of N-oxides are obtained, the 1-N-oxides and 3-N-oxides can be separated by chromatography, or by selective crystallization from a suitable solvent, for example from a mixture of ethanol/ether.

Preparation of Compounds I where $R^1$ is Hydroxyalkyl or Alkenyl from N-Oxides of Formula I The preparation of compounds of Formula I where $R^1$ is hydroxyalkyl or alkenyl from N-oxides of Formula I is shown below in Reaction Scheme XII.

REACTION SCHEME XII

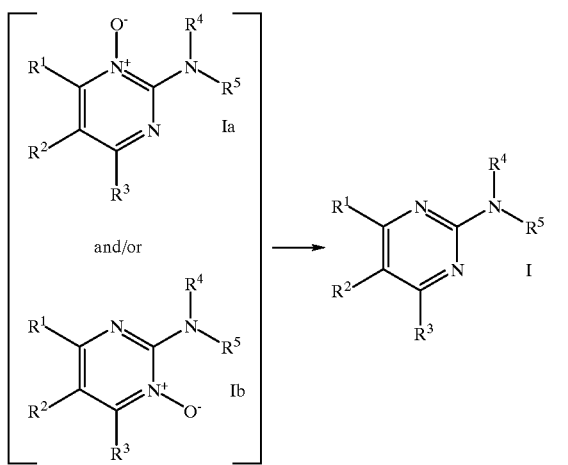

where $R^1$ is alkyl in Formulae Ia and Ib, and $R^1$ is hydroxyalkyl or alkenyl in Formula I; and $R^2$, $R^3$, $R^4$ and $R^5$ are as defined in the Summary of the invention.

Preparation of I from N-Oxides of Formula I

An N-oxide of Formula I where $R^1$ is alkyl is reacted with an excess of a carboxylic anhydride, preferably trifluoroacetic anhydride, in an inert solvent, preferably methylene chloride. The reaction is carried out at a temperature of about 5 to 60° C., preferably about 25° C., for about 10 to 60 hours, preferably 48 hours. After work-up with an aqueous base, such as ammonium hydroxide in alcohol or sodium hydroxide, the product, a mixture of compounds of Formula I where $R^1$ is 6-hydroxyalkyl and 6-alkenyl, is isolated and purified by conventional means, preferably by chromatography.

Conversion of Compounds of Formula I to Other Compounds of Formula I

The compounds of Formula I where $R^1$, $R^2$ and $R^3$ are as defined in the Summary of the Invention, and $R^4$ and $R^5$ are hydrogen may be converted to other compounds of Formula I by replacing one or both hydrogens of $R^4$ and $R^5$ with other groups:

A. For example, a compound of Formula I where $R^4$ and $R^5$ are hydrogen is reacted with an acylating agent, preferably acetic anhydride, optionally in the presence of catalyst such as 4-dimethylaminopyridine. The reaction mixture is carried out at a temperature range of 0° to 100° C., for about 4 hours. A diacyl product is isolated by conventional means, dissolved in a protic solvent, such as methanol, and treated with an inorganic base such as sodium bicarbonate, for about 1 to 24 hours. The resulting monoacyl product, a compound of Formula I where $R^4$ is acyl and $R^5$ is hydrogen, is isolated and purified by conventional means.

B. For example, a compound of Formula I where $R^4$ and $R^5$ are hydrogen is reacted with a tertiary amine, preferably triethyl amine, and a sulfonylating agent, preferably methanesulfonyl chloride. The reaction is carried out in an inert organic solvent such as dichloromethane, at a temperature of about 0°, for about 5 minutes to 3 hours, preferably 30 minutes. The resulting bis-methanesulfonyl product, a compound of Formula I where $R^4$ and $R^5$ are —$SO_2R^{12}$, is isolated and purified by conventional means.

C. For example, a compound of Formula I where $R^4$ is —$SO_2R^{12}$ and $R^5$ is hydrogen, may be prepared from the bis-sulfonyl product previously described above in Section B. The reaction is carried out under basic conditions, preferably in the presence of sodium hydroxide, in a protic organic solvent such as methanol, at about room temperature for about 30 minutes to 3 hours, preferably 1 hour. The resulting mono-sulfonyl product, a compound of Formula I where $R^4$ is —$SO_2R^{12}$ and $R^5$ is hydrogen, is isolated and purified by conventional means.

D. For example, a compound of Formula I where $R^4$ and $R^5$ are hydrogen is reacted with an isocyanate derivative, preferably phenyl isocyanate, in an inert organic solvent, preferably benzene, at reflux temperature for about 10 to 60 hours, preferably 48 hours. The resulting reaction product, a compound of Formula I where $R^4$ is amido and $R^5$ is hydrogen, is isolated and purified by conventional means.

Alternative Conversion of Compounds of Formula I to Other Compounds of Formula I The compounds of Formula I where $R^1$, $R^2$ are as defined in the Summary of the Invention, $R^3$ is an aryl substituted with a halo substituent, and $R^4$ and $R^5$ are hydrogen may be converted to other compounds of Formula I by replacing the halo subsituent with other groups:

A. For example, a compound of Formula I where $R^3$ is aryl substituted with a halo substituent, and $R^4$ and $R^5$ are hydrogen, is reacted with an alkali metal azide, preferably sodium azide, in an aprotic polar solvent, preferably N-methyl pyrrolidinone. The reaction mixture brought to a temperature of about 100 to 200° C., preferably about 160° C., under an inert atmosphere for about 5 to 30 hours, preferably about 16 hours. The reaction product, a compound of Formula I where $R^3$ is aryl substituted with an amino substituent, is isolated and purified by conventional means.

B. For example, a compound of Formula I where $R^3$ is aryl substituted with a halo substituent, and $R^4$ and $R^5$ are hydrogen, is reacted with excess alkali metal thioalkyloxide, preferably sodium thiomethoxide, in an aprotic polar solvent, preferably dimethyl sulfoxide. The reaction mixture is carried out at about room temperature for about 10 minutes to 10 hours, preferably about 4 hours. The reaction product, a compound of Formula I where $R^3$ is aryl substituted with a lower thioalkyl substituent, is isolated and purified by conventional means.

Alternative Conversion of Compounds of Formula I to Other Compounds of Formula I The compounds of Formula I where $R^1$, $R^3$, $R^4$, and $R^5$ are as defined in the Summary of the Invention, and $R^2$ is hydrogen may be converted to other compounds of Formula I by replacing the hydrogen of $R^2$ with other groups:

For example, a compound of Formula I where $R^2$ is hydrogen, is reacted with a halogen, preferably bromine, in the presence of a metal catalyst, preferably iron powder, in an inert organic solvent such as carbon tetrachloride. The reaction is carried out at about room temperature for about 10 minutes to 10 hours, preferably about 1 hour. The reaction product, a compound of Formula I where $R^2$ is halo, is isolated and purified by conventional means.

Alternative Conversion of Compounds of Formula I to Miscellaneous Compounds of Formula I The compounds of Formula I where $R^1$, $R^2$, and $R^3$ are as defined in the Summary of the Invention, $R^4$ is lower alkyl substituted by amino or carboxy group, and $R^5$ is hydrogen may be converted to other compounds of Formula I by converting $R^4$ to other groups:

A. For example, a compound of Formula I where $R^4$ is lower alkyl substituted by amino and $R^5$ is hydrogen, is dissolved in an inert organic solvent, such as diethyl ether and is reacted with a sulfonylating agent, preferably methanesulfonyl chloride. The reaction is carried out at about room temperature for 10 minutes to 10 hours, preferably 1 hour. The sulfonylated reaction product, a compound of Formula I where $R^4$ is lower alkyl substituted by sulfonamido and $R^5$ is hydrogen, is isolated and purified by conventional means.

B. For example, a compound of Formula I where $R^4$ is lower alkyl substituted by a carboxylic acid ester and $R^5$ is hydrogen, is dissolved in a protic solvent solution containing a primary or secondary amine, preferably an ethanolic methyl amine solution, and sonicated for about 30 minutes to 10 hours, preferably 3 hours. The amido reaction product, a compound of Formula I where $R^4$ is lower alkyl substituted by amido, is isolated and purified by conventional means.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of Formula I are basic, and thus may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of Formula I may be converted to the corresponding free bases by treatment with at least a stoichiometric amount of a suitable base such as sodium or potassium hydroxide, potassium carbonate, sodium bicarbonate, ammonia, and the like.

Preferred Processes

In summary, compounds of Formula I are prepared according to the following last steps:

1. A process for preparing compounds of Formula I comprises:

reacting a compound of the formula:

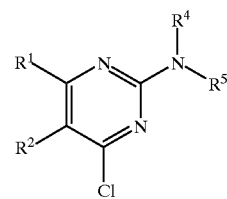

where $R^1$ and $R^2$ are as defined in the Summary of the Invention, and $R^4$ and $R^5$ are hydrogen or lower alkyl;

with a boronic acid derivative of formula (5), i.e., $R^3B(OH)_2$, where $R^3$ is as defined in the Summary of the Invention.

2. Alternatively, a process for preparing compounds of Formula I comprises:

reacting a compound of the formula:

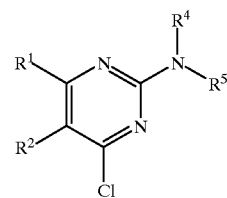

where $R^1$ and $R^2$ are as defined in the Summary of the Invention, and $R^4$ and $R^5$ are hydrogen or lower alkyl;

with a boron complex of formula (7), i.e., $R^3B(OCH_3)_2$, where $R^3$ is as defined in the Summary of the Invention.

3. Alternatively, a process for preparing compounds of Formula I comprises:

reacting a compound of the formula:

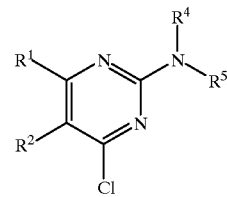

where $R^1$ and $R^2$ are as defined in the Summary of the Invention, and $R^4$ and $R^5$ are hydrogen or lower alkyl;

with a compound of the formula (8):

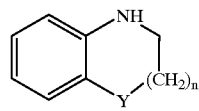

where Y and n are as defined in the Summary of the Invention.

4. Alternatively, a process for preparing compounds of Formula I comprises:

reacting a compound of the formula:

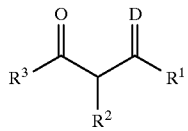

where $R^1$, $R^2$, and $R^3$ are as defined in the Summary of the Invention;
with a compound of the formula $NH_2C(:NH)NR^4R^5$ (formula (2)), where $R_4$ and $R_5$ are as defined in the Summary of the Invention.

5. Alternatively, a process for preparing compounds of Formula I comprises:
reacting a compound of the formula:

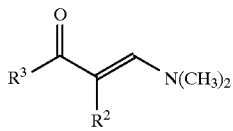

where $R^2$ and $R^3$ are as defined in the Summary of the Invention;
with a compound of the formula $NH_2C(:NH)NR^4R^5$ (formula (2)), where $R_4$, and $R_5$, are as defined in the Summary of the Invention.

6. Alternatively, a process for preparing compounds of Formula I comprises:
reacting a compound of the formula:

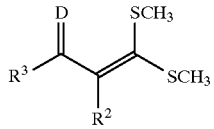

where $R^3$ is as defined in the Summary of the Invention.
with a compound of the formula $NH_2C(:NH)NR^4R^5$ (formula (2)), where $R_3$ is as defined in the Summary of the Invention.

7. Alternatively, a process for preparing compounds of Formula I comprises:
reacting a compound of the Formula I where $R^1$ is chloro:

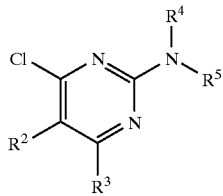

where $R^2$ and $R^3$ are as defined in the Summary of the Invention, and $R^4$ and $R^5$ are hydrogen or lower alkyl; with
A) a reducing agent, to give a compound of Formula I where $R^1$ is hydrogen; or
B) a primary or secondary amine of formula $HNR^6R^7$, where $R^6$ and $R^7$ are as defined in the Summary of the Invention, to give a compound of Formula I where $R^1$ is —$NR^6R^7$.

8. Alternatively, a process for preparing compounds of Formula I comprises:

reacting a compound of the formula:

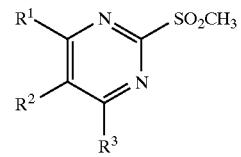

where $R^1$, $R^2$ and $R^3$ are as defined in the Summary of the Invention, with a secondary amine of formula $HNR^4R^5$, where $R^4$ and $R^5$ are as defined in the Summary of the Invention, to give a compound of Formula I, where $R^4$ and $R^5$ are as defined in the Summary of the Invention.

9. Alternatively, a process for preparing compounds of Formula I where $R^1$ is hydroxyalkyl or alkenyl comprises:
reacting an N-oxide of a compound of Formula I where $R^1$ is alkyl with a carboxylic anhydride to give a compound of Formula I.

10. Alternatively, a process for preparing compounds of Formula I comprises:
reacting a compound of Formula I with an oxidizing agent to give an N-oxide of a compound of Formula I, or:
reacting a compound of Formula I with a strong acid to give a pharmaceutically acceptable salt of a compound of Formula I.

Utility and Administration

General Utility

The compounds of this invention are selective 5-HT 2B receptor antagonists. Affinity for the 5-$HT_{2B}$ receptors was demonstrated using an in vitro binding assay utilizing cloned 5-$HT_{2B}$ receptors radiolabelled with [H]-5HT, as shown in Example 22 infra. Selectivity for the 5-$HT_{2B}$ receptor was shown by counter screening at 5-$HT_{2A}$ and 5-$HT_{2C}$, receptors (for details see Example 23, infra.). Antagonist properties were determined in rat stomach fundus longitudinal muscle (for further details see Example 24, infra.).

Accordingly, the compounds of this invention are useful for treating diseases which can be ameliorated by blockade of 5-$HT_{2B}$ receptors. Because of the similarities in the pharmacology of ligand interactions at 5-$HT_{2C}$ and 5-$HT_{2B}$ receptors many of the therapeutic targets that have been proposed for 5-$HT_{2C}$ receptor antagonists are also targets for 5-$HT_{2B}$ receptor antagonists. In particular, several clinical observations suggest a therapeutic role for 5-$HT_{2B}$ receptor antagonists in the prevention of migraine, in that mobilization of 5-HT into the plasma is believed to be a precipitating factor in migraine. Additionally, non-selective 5-$HT_{2B}$ receptor agonists provoke migraine attacks in susceptible individuals, and non-selective 5-$HT_{2B}$ receptor antagonists are effective in preventing the onset of migraine (see Kalkman, *Life Sciences* 1994, 54, 641–644).

Experimental evidence indicates that the compounds of the present invention are useful in the treatment of pain, including acute, chronic, neuropathic, inflammatory, and cancer pain, particularly inflammatory pain. (See Example 27, infra.) 5-HT (serotonin) plays a key role in the regulation of transmission of nociceptive information at various levels of the peripheral and central nervous systems. (See Richardson, B. P., "Serotonin and Pain", *Ann. N.Y. Acad. Sci.*, 1990, 600, 511–520). Moreover, neuronal systems counting 5-HT are involved not only in the regulation of nociceptive input at the spinal and supraspinal level, but in mediating the nociceptive action of other analgesics including the opiates. 5-HT is a mediator of sensitization of nerve terminal nociceptors that may occur in the genesis of pain associated with inflammation. The 5-HT2B receptor is highly sensitive to activation by 5-HT and specific blockade by selective 5-HT$_{2B}$ antagonists may provide a novel avenue toward analgesia therapy.

Experimental evidence supports a therapeutic role for 5-HT$_{2B}$ receptor antagonists in treating hypertension. In hypertension, one of the most profound increases in vascular responsiveness is observed for serotonin. Two lines of evidence imply that this results from a switch in the receptor mediating vasoconstriction from predominantly 5-HT$_{2A}$ to predominantly 5-HT$_{2B}$. First, serotonin induced contractions of isolated blood vessels from hypertensive animals become resistant to block by selective 5-HT$_{2A}$ receptor antagonists, but remain sensitive to non-selective 5-HT$_2$ receptor antagonists. Second, there is an increase in 5-HT$_{2B}$ receptor mRNA in vessels from hypertensive animals (see Watts et al., *J. Pharmacol. Exp. Ther.* 1996, 277, 1103–13 and Watts et al., *Hypertension* 1995, 26, 1056–1059). This hypertension-induced shift in the population of receptor subtype mediating constrictor responses to 5-HT suggests that selective block of vasoconstrictor 5-HT$_{2B}$ receptors may be of therapeutic benefit in the treatment of hypertension.

Clinical and experimental evidence support a therapeutic role for 5-HT$_{2B}$ receptor antagonists in treating disorders of the gastrointestinal track, in particular irritable bowel syndrome (IBS). Although the pathology underlying IBS remains unclear, there is a well-established implied role for the involvement of serotonin. Thus, meals with a high serotonin content can exacerbate symptoms in some patients (see Lessorf, *Scand. J. Gastroenterology* 1985, 109, 117–121), while in pre-clinical studies, serotonin has been shown directly to sensitize visceral sensory neurons resulting in an enhanced pain response similar to that observed in IBS (see Christian et al., *J. Applied Physiol.* 1989, 67, 584–591 and Sanger et al., *Neurogastroenterology and Motility* 1996, 8, 319–331). The possibility that 5-HT$_{2B}$ receptors play a crucial role in the sensitizing actions of serotonin are suggested by several lines of evidence. First, 5-HT$_{2B}$ receptors are present in the human intestine (see Borman et al., *Brit. J. Pharmacol.* 1995, 114, 1525–1527 and Borman et al., *Ann. of the New York Acad. of Sciences* 1997, 812, 222–223). Second, activation of 5-HT$_{2B}$ receptors can result in the production of nitric oxide, an agent capable of sensitizing sensory nerve fibers (see Glusa et al., *Naunyn-Schmied. Arch. Pharmacol.* 1993, 347, 471–477 and Glusa et al., *Brit. J. Pharmacol.* 1996, 119, 330–334). Third, poorly selective drugs which display high affinity for the 5-HT$_{2B}$ receptor are clinically effective in reducing the pain associated with IBS and related disorders (see Symon et al., *Arch. Disease in Childhood* 1995, 72, 48–50 and Tanum et al., *Scand. J. Gastroenterol.* 1996, 31, 318–325). Together these findings suggest that a selective 5-HT$_{2B}$ receptor antagonist will attenuate both the gastrointestinal pain and abnormal motility associated with IBS.

Clinical and experimental evidence support a therapeutic role for 5-HT$_{2B}$ receptor antagonists in treating restenosis. Angioplasty and bypass-grafting are associated with restenosis which limits the efficacy of these procedures. Platelet-rich thrombus formation is the predominant cause of acute occlusion whereas serotonin, among other platelet-derived mediators, is thought to contribute to late restenosis (see Barradas et al., *Clinica Chim. Acta* 1994, 230, 157–167). This late restenosis involves proliferation of the vascular smooth muscle. Two lines of evidence implicate a role for 5-HT$_{2B}$ receptors in this process. First, serotonin displays a potent mitogenic activity in cultured smooth muscle and endothelial cells via activation of 5-HT$_2$ receptors (see Pakala et al., *Circulation* 1994, 90, 1919–1926). Second, this mitogenic activity appears to be mediated via activation of a tyrosine kinase second messenger pathway involving mitogen activated protein kinase (MAPK) (see Lee et al., *Am. J. Physiol.* 1997, 272(1 pt 1), C223–230 and Kelleher et al., *Am. J. Physiol.* 1995, 268(6 pt 1), L894–901). The recent demonstration that 5-HT$_{2B}$ receptors couple to MAPK, coupled with the high affinity of serotonin for this receptor subtype, indicates that a selective 5-HT$_{2B}$ receptor antagonist may afford protection against restenosis of autografted blood vessels or of vessels following angioplasty.

Clinical and experimental evidence support a therapeutic role for 5-HT$_{2B}$ receptor antagonists in treating asthma and obstructive airway disease. Abnormal proliferation of airways smooth muscle, together with hyper-reactivity of the smooth muscle to constrictor stimuli including serotonin, plays a significant role in the pathogenesis of human airway disease such as asthma and bronchial pulmonary dysplasia (see James et al., *Am. Review of Respiratory Disease* 1989, 139, 242–246 and Margraf et al., *Am. Review of Respiratory Disease* 1991, 143, 391–400). In addition to other subtypes of serotonin receptor, 5-HT$_{2B}$ receptors are present in bronchial smooth muscle (see Choi et al., *Febs Letters* 1996, 391, 45–51) and have been shown to stimulate smooth muscle mitogenesis in airways smooth muscle (see Lee et al., *Am. J. Physiol.* 1994, 266, L46–52). Since elevated concentrations of circulating free serotonin are closely associated with clinical severity and pulmonary function in symptomatic asthmatics, serotonin may play an important role in the pathophysiology of acute attacks (see Lechin et al., *Ann. Allergy, Asthma, Immunol.* 1996, 77, 245–253). These data suggest that a selective antagonist of 5-HT$_{2B}$ receptors in airways smooth muscle may therefore be useful in preventing airways constriction resulting from the elevated levels of circulating serotonin and prevent proliferation of the airways smooth muscle that contributes to the long-term pathology of this disease.

Experimental evidence supports a therapeutic role for 5-HT$_{2B}$ receptor antagonists in treating prostatic hyperplasia. Obstruction of the urinary tract can occur as a result of prostatic hyperplasia and excessive prostatic constriction of the urethra. This in turn leads to diminished urinary flow rates and an increased urgency and frequency of urination. 5-HT$_{2B}$ receptors are present in the human prostate (see Kursar et al., *Mol. Pharmacol.* 1994, 46, 227–234) and a receptor with the pharmacological attributes of this receptor subtype mediates contraction of the tissue (see Killam et al., *Eur. J. Pharmacol.* 1995, 273, 7–14). Some drugs effective in the treatment of benign prostatic hyperplasia block 5-HT mediated contractions of the prostate (see Noble et al., *Brit. J. Pharmacol.* 1997, 120, 231–238). 5-HT$_{2B}$ receptors mediate smooth muscle and fibrotic hyperplasia (see Launay et al., *J. Biol. Chem.* 1996, 271, 3141–3147) and serotonin is mitogenic in the prostate (see Cockett et al., *Urology* 1993, 43, 512–519), therefore a selective 5-HT$_{2B}$ receptor antagonist may have utility not only in mitigating the excessive prostatic constriction, but also in preventing progression of tissue hyperplasia.

Clinical and experimental evidence support a therapeutic role for 5-HT$_{2C}$ receptor antagonists in treating anxiety. The 5-HT$_{2C}$ receptor agonist 1-(3-chlorophenyl)piperazine (mCPP) when administered to human volunteers causes anxiety (see Charney et al., *Psychopharmacology* 1987, 92, 14–24). MCPP also produces anxiogenic effects in rat, social interaction (SI) and elevated X-maze models of anxiety, which effects are blocked by non-selective 5-HT$_{2C/2A}$ receptor antagonists but not by selective 5-HT$_{2A}$ receptor antagonists (see Kennett et al., *Eur. J. Pharmacol.* 1989, 164, 445–454 and Kennett 1993, supra.). In addition, non-selective 5-HT$_{2C/2A}$ receptor antagonists by themselves produce anxiolytic effects in the SI and Geller Seifter conflict tests, while selective 5-HT$_{2A}$ receptor antagonists do not share this property. This therapeutic target for 5-HT$_{2C}$ receptor antagonists is equally a target for 5-HT$_{2B}$ receptor antagonists.

Furthermore, mCPP when administered to panic disorder patients or obsessive compulsive disorder patients increases levels of panic and/or anxiety (see Charney et al. 1987, supra. and Zohar et al., *Arch. Gen. Psychiat.* 1987, 44, 946–951). Thus, current evidence support the application of selective 5-HT$_{2C}$ receptor antagonists for treating generalized anxiety disorder, panic disorder and obsessive compulsive disorder. These therapeutic targets for 5-HT$_{2C}$ receptor antagonists are equally targets for 5-HT$_{2B}$ receptor antagonists.

Anxiolytic activity can be determined experimentally by the art-recognized Crawley and Goodwin two-compartment exploratory model (e.g., see Kilfoil et al., *Neuropharmacology* 1989, 28(9), 901–905). In brief, the method measures the extent a compound affects the natural anxiety of mice in a novel, brightly lighted area (for further details see Example 25, infra.).

Clinical and experimental evidence support a therapeutic role for selective 5-HT$_{2C}$ receptor antagonists in treating chemical dependency. The 5-HT$_{2C}$ receptor agonist mCPP induces a craving for alcohol in abstaining alcoholics (see Benkelfat et al., *Arch. Gen. Psychiat.* 1991, 48, 383). In contrast, the non-selective 5-HT$_{2C/2A}$ receptor antagonist ritanserin reduces alcohol preference in rats (see Meert et al., *Drug Development Res.* 1991, 24, 235–249), while the selective 5-HT$_{2A}$ receptor antagonist ketanserin has no affect on preference for alcohol (see Kennett et al., *J. Psychopharmacol.* 1992, Abstr. A26). Ritanserin also reduces both cocaine and fentanyl preference in rat models of addiction (see Meert et al., *Drug Development Res.* 1991, 25, 39–53 and Meert et al., *Drug Development Res.* 1991, 25, 55–66). Clinical studies show that ritanserin decreases alcohol intake in chronic alcoholics (see Monti et al., *Lancet* 1991, 337, 60) and is useful in patients withdrawing from other drugs of abuse (see Sadzot at al., *Psychopharmacology,* 1989, 98, 495–499). Thus, current evidence support the application of selective 5-HT$_{2C}$ receptor antagonists for treating alcoholism and addiction to other drugs of abuse. This therapeutic target for 5-HT$_{2B}$ receptor antagonists is equally a target for 5-HT$_{2B}$ receptor antagonists.

Ameliorating effects of compounds during withdrawal from drugs of abuse can be determined experimentally by the mouse, withdrawal anxiety test, an accepted assay (e.g., see Carboni et al., *Eur. J. Pharmacol.* 1988, 151, 159–160). This procedure utilizes the exploratory model described above to measure the extent a compound ameliorates the symptoms of withdrawal that occur after chronically treating with an addictive substance and then abruptly ceasing the treatments (for further details see Example 26, infra.).

Clinical evidence supports a therapeutic role for selective 5-HT$_{2C}$ receptor antagonists in treating depression. For example, non-selective 5-HT$_{2C/2A}$ receptor antagonists show clinical efficacy in treating depression (see Murphy, *Brit. J. Pharmacol.* 1978, 5, 81S-85S; Klieser et al., *Pharmacopsychiat.* 1988, 21, 391–393; and Camara, *Biol. Psychiat.* 1991, 29, 201A). Furthermore, experimental results suggest that the mechanism by which conventional antidepressant drugs exert their therapeutic efficacy is through adaptive changes in the serontinergic system (see Anderson, *Life Sci.* 1983, 32, 1791–1801). For example, chronic treatment with monamine oxidase inhibitors reduce mCPP-induced/5-HT$_{2C}$ mediated functional responses in a variety of paradigms. Similar effects are exhibited by selective 5-HT reuptake inhibitors. These findings suggest that treatments which enhance extraneuronal 5-HT levels desensitize 5-HT$_{2C}$ receptor function which in turn causes, or contributes to, antidepressant activity (see Kennett 1993, supra.). This therapeutic target for 5-HT$_{2C}$ receptor antagonists is equally a target for 5-HT$_{2B}$ receptor antagonists.

Clinical evidence supports a therapeutic role for 5-HT$_{2C}$ receptor antagonists in treating sleep disorders. The 5-HT$_{2C}$ receptor agonist mCPP when administered to human volunteers reduces total sleep time, sleep efficiency, slow wave sleep (SWS) and rapid eye movement sleep (see Lawlor et al., *Biol. Psychiat.* 1991, 29, 281–286). In contrast, the non-selective 5-HT$_{2C/2A}$ receptor antagonist ritanserin increases SWS, reduces sleep onset latency and improves subjective sleep quality in healthy volunteers (see Idzikowski et al., *Brain Res.* 1986, 378, 164–168; Idzikowski et al., *Psychopharmacology* 1987, 93, 416–420; Declerck et al., *Curr. Therap. Res.,* 1987, 41, 427–432; and Adam et al., *Psychopharmacol.* 1989, 99, 219–221). Thus, given the opposing effects of 5-HT$_{2C}$ receptor stimulation and 5-HT$_{2C}$ receptor antagonism, selective 5-HT$_{2C}$ receptor antagonists could be of particular therapeutic value in treating sleep disorder (see Kennett 1993, supra.). This therapeutic target for 5-HT$_{2C}$ receptor antagonists is equally a target for 5-HT$_{2B}$ receptor antagonists.

Clinical evidence supports a therapeutic role for 5-HT$_{2C}$ receptor antagonists in feeding disorders. Non-specific 5-HT$_{2C/2A}$ receptor antagonists are shown to produce increased appetite and weight gain. Thus, there is some clinical evidence to support the application of selective 5-HT$_{2C}$ receptor antagonists for the treatment of anorexia nervosa. This therapeutic target for 5-HT$_{2C}$ receptor antagonists is equally a target for 5-HT$_{2B}$ receptor antagonists.

Experimental evidence supports a therapeutic role for 5-HT$_{2C}$ receptor antagonists in treating priapism (see Kennett, *Curr. Opin. Invest. Drugs* 1993, 2, 317–362). MCPP produces penile erections in rats, which effect is blocked by non-selective 5-HT$_{2C/2A}$ receptor antagonists but not by selective 5-HT$_{2A}$ receptor antagonists (see Hoyer, *Peripheral actions of 5-HT* 1989, Fozard J. (ed.), Oxford University Press, Oxford, 72–99). This therapeutic target for 5-HT$_{2C}$ receptor antagonists is equally a target for 5-HT$_{2B}$ receptor antagonists.

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dose for oral, parenteral and otherwise systemic routes of administration is in the range of 0.01–20 mg/kg/day, preferably 0.1–10 mg/kg/day. For an average 70 kg human, this would amount to 0.7–1400 mg per day, or preferably 7–700 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. The composition or formulation to be administered will, in any event, contain a quantity of the active compound(s) in an amount effective to alleviate the symptoms of the subject being treated.

Dosage forms or compositions containing active ingredient (compounds of Formula I or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%–95% active ingredient, more preferably 2–50%, most preferably 5–8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as, for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained (see, e.g., U.S. Pat. No. 3,710,795).

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1% to 10%, most preferably 0.5% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.5% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 19th Edition, 1995.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Examples 16–21.

EXAMPLES

The following preparation and examples illustrate the invention but are not intended to limit its scope.

PREPARATION 1

Preparation of Compounds of Formula (3)

A. Preparation of (3) where $R^1$ is tert-Butyl and $R^2$ is Hydrogen

Methyl 4,4-dimethyl-3-oxopentanoate (15.82 g) and guanidine carbonate (20.0 g) were mixed in 80 mL of ethanol, and the solution refluxed for 16 hours. The reaction mixture was concentrated to 50 mL by removal of solvent under reduced pressure, and 20 mL of water was added. The remaining mixture was acidified to pH 5 with acetic acid, affording a white precipitate. The precipitate was collected by filtration, washed with water, and dried in a vacuum oven to give 2-amino-4-hydroxy-6-tert-butylpyrimidine (12.6 g), m.p. 285–288° C. (dec.).

B. Preparation of (3) where $R^2$ is Hydrogen, varying $R^1$

Similarly, replacing methyl 4,4-dimethyl-3-oxopentanoate with:
ethyl 3-oxopentanoate;
ethyl 4-methyl-3-oxopentanoate;
ethyl 3-cyclobutyl-3-oxopropionate;
ethyl 3-cyclopentyl-3-oxopropionate;
ethyl 4-methyl-3-oxohexanoate;
ethyl 2-methyl-3-oxobutanoate;
ethyl 3-oxo-4-phenylpentanoate;
ethyl 3-cyclopropyl-3-oxopropionate;
ethyl 2-fluoro-3-oxobutanoate;
ethyl 2-aminocarbonylacetate;
ethyl 4,4,4-trifluoro-3-oxobutanoate; and
ethyl 3-phenyl-3-oxopropionate;
(in some syntheses the methyl ester was used instead of the ethyl ester; both work equally well):
and following the procedures of Preparation 1A above, the following compounds of formula (3) were prepared:
2-amino-6-ethyl-4-hydroxypyrimidine;
2-amino-4-hydroxy-6-isopropylpyrimidine, m.p. 238–241° C.;
2-amino-6-cyclobutyl-4-hydroxypyrimidine, m.p. 253–254° C.;
2-amino-6-cyclopentyl-4-hydroxypyrimidine, m.p. 237–241° C. (dec.);
2-amino-6-(but-2-yl)-4-hydroxypyrimidine, m.p. 195–198° C.;
2-amino-5,6-dimethyl-4-hydroxypyrimidine;
2-amino-6-benzyl-4-hydroxypyrimidine;
2-amino-6-cyclopropyl-4-hydroxypyrimidine;
2-amino-5-fluoro-4-hydroxy-6-methylpyrimidine;
2,6-diamino-4-hydroxypyrimidine;
2-amino-4-hydroxy-6-trifluoromethylpyrimidine; and
2-amino-4-hydroxy-6-phenylpyrimidine.

C. Similarly, optionally replacing methyl 4,4-dimethyl-3-oxopentanoate with other compounds of formula (1), and optionally replacing guanidine carbonate with other compounds of formula (2), and following the procedures of Preparation 1A above, other compounds of formula (3) are prepared.

PREPARATION 2

Preparation of Compounds of Formula (4)

A. Preparation of (4) where $R^1$ is tert-Butyl and $R^2$ is Hydrogen

2-Amino-4-hydroxy-6-tert-butylpyrimidine (8.35 g) was dissolved in 50 mL of phosphorus oxychloride and the solution refluxed for 2 hours. Excess phosphorus oxychloride was removed under vacuum and the residue dissolved in 100 mL of ethanol. The solution was adjusted to pH 8 with ice-cold concentrated ammonium hydroxide, and solvent removed under reduced pressure. The residue was filtered to give a white solid, which was recrystallized from ethanol-water to give 2-amino-4-chloro-6-tert-butylpyrimidine (3.66 g), m.p. 87.7–88.9° C.

B. Similarly, replacing 2-amino-4-hydroxy-6-tert-butylpyrimidine with other compounds of formula (3) and following the procedures of Preparation 2A above, the following compounds of formula (4) were prepared:
2-amino-4-chloro-6-ethylpyrimidine;
2-amino-4-chloro-6-isopropylpyrimidine, m.p. 94–97° C.;
2-amino-4-chloro-6-cyclopropylmethylpyrimidine, m.p. 116.5–120.0° C.;
2-amino-4-chloro-6-cyclobutylpyrimidine, m.p. 98–99° C.;
2-amino-6-(but-2-yl)-4-chloropyrimidine, m.p. 63–65° C.;
2-amino-4-chloro-6-cyclopentylpyrimidine, m.p. 101.5–103° C.
2-amino-4-chloro-5,6-dimethylpyrimidine;
2-amino-6-benzyl-4-chloropyrimidine;
2-amino-4-chloro-6-cyclopropylpyrimidine;
2-amino-4-chloro-5-fluoro-6-methylpyrimidine;
2,6-diamino-4-chloropyrimidine;
2-amino-4-chloro-6-trifluoromethylpyrimidine; and
2-amino-4-chloro-6-phenylpyrimidine.

C. Similarly, replacing 2-amino-4-hydroxy-6-tert-butylpyrimidine with other compounds of formula (3), and following the procedures of Preparation 2A above, other compounds of formula (4) are prepared.

PREPARATION 3

Preparation of Compounds of Formula (9)

A. Preparation of (9) where $R^3$ is 4.7-Difluoronapth-1-yl and $R^2$ is Hydrogen 1,6-Difluoronaphthalene (0.164 g, 1.0 mmol) was dissolved in 1,2-dichloroethane (5 mL) and cooled to 0° C. Aluminum trichloride (0.264 g, 2.0 mmol) was added as a solid to the solution. Acetic anhydride (0.1 mL, 1.0 mmol) was added slowly over 20 minutes to the solution while maintaining a temperature of 0° C. The reaction was poured onto ice-cold 10% aqueous hydrochloric acid and extracted with methylene chloride (2×10 mL). The organic layer was dried over sodium sulfate, concentrated, and purified by column chromatography to give 1-(4,7-difluoronaphth-1-yl)-ethanone as an oil (0.165 g, 80%).

B. Similarly, replacing 1,6-difluoronaphthalene with other compounds of formula $R^3$, and following the procedures of Preparation 3 above, other compounds of formula (9) are prepared.

PREPARATION 4

Preparation of Compounds of Formula (15)

A. Preparation of (15) where $R^1$ is methyl and $R^2$ is Hydrogen

S-Methylisothiourea (22.26 g, 160 mmol) was added to a solution of sodium carbonate (16.9 g, 160 mmol) in water (50 mL) and stirred at room temperature until complete dissolution of the S-methylisothiourea. Ethyl acetoacetate (10.41 g, 80 mmol) was added to the mixture in one portion. After stirring for 60 hours at room temperature, the reaction was neutralized with acetic acid precipitating a white solid. The solid was collected, washed with water, and dried in vacuo to give 4-hydroxy-6-methyl-2-(methylthio) pyrimidine (9.38 g, 75%), m.p. 218–221° C.

B. Preparation of (15) where $R^2$ is Hydrogen, varying $R^1$

Similarly, replacing ethyl acetoacetate with ethyl-4-methyl-3-oxopentanoate or methyl-4,4-dimethyl-3-oxopentanoate, and following the procedures of Preparation 4A above, the following compounds of formula (15) were prepared:
4-hydroxy-6-isopropyl-2-(methylthio)pyrimidine; and
6-tert-butyl-4-hydroxy-2-(methylthio)pyrimidine.

C. Preparation of (15) where $R^2$ is Hydrogen, varying $R^1$

Similarly, replacing ethyl acetoacetate with other compounds of formula (1) and following the procedures of Preparation 4A above, other compounds of formula (15) are prepared.

PREPARATION 5

Preparation of Compounds of Formula (16)

A. Preparation of (16) where $R^1$ is Methyl and $R^2$ is Hydrogen

4-Hydroxy-6-methyl-2-(methylthio)pyrimidine (9.20 g, 59 mmol) and phosphorous oxychloride (60 mL) were combined and refluxed for 3 hours. The reaction mixture was cooled to room temperature and poured onto crushed ice. The resultant aqueous mixture was extracted with ethyl acetate; and the organic layer washed with saturated aqueous sodium bicarbonate followed by a water wash, dried over magnesium sulfate, and dried in vacuo to give 4-chloro-6-methyl-2-(methylthio)pyrimidine (8.27 g, 80%), m.p. 37–38° C.

B. Similarly, replacing 4-hydroxy-6-methyl-2-(methylthio)pyrimidine with other compounds of formula (15), and following the procedures of Preparation 5A above, the following compounds of formula (16) were prepared:
4-chloro-6-isopropyl-2-(methylthio)pyrimidine, b.p. 127–128° C. @ 0.5 torr; and
6-tert-butyl-4-chloro-2-(methylthio)pyrimidine, m.p. 46–48° C.

C. Similarly, replacing 4-hydroxy-6-methyl-2-(methylthio)pyrimidine with other compounds of formula (15) and following the procedures of Preparation 5A above, other compounds of formula (16) are prepared.

PREPARATION 6

Preparation of Compounds of Formula (17)

A. Preparation of (17) where $R^1$ is Isopropyl, $R^2$ is Hydrogen, and $R^3$ is 4-Fluoro-1-naphthyl A stirred solution of 1-bromo-4-fluoronaphthalene (4.95 g) in 100 mL tetrahydrofuran was cooled to –80° C., stirred and 2.5M n-butyllithium (10 mL) was added dropwise. The mixture was stirred for 30 minutes, then trimethoxyborane (3 mL) added, the mixture stirred for 1 hour, then allowed to warm to room temperature, and solvent removed under reduced pressure. To this residue was added benzene (100 mL), 4-chloro-6-isopropyl-2-(methylthio)pyrimidine (4.04 g), tetrakis(triphenylphosphine)palladium(0) (500 mg), and sodium carbonate (20 mL of 2M), was heated to reflux (about 80° to 90° C.) for 14 hours. The mixture was filtered, and solvent was removed under reduced pressure. The residue was chromatographed on silica gel, eluting with 2% ethyl acetate/hexane, to give impure 4-(4-fluoronaphth-1-yl)-6-isopropyl-2-(methylthio)pyrimidine (4.87 g), which was used in the next reaction with no further purification.

B. Similarly, replacing 4-chloro-6-isopropyl-2-(methylthio)pyrimidine with other compounds of formula (16), and following the procedures of Preparation 5A above, the following compounds of formula (17) were prepared:
4-(4-fluoronaphth-1-yl)-6-methyl-2-(methylthio) pyrimidine, m.p. 140–142° C.; and
4-(4-fluoronaphth-1-yl)-6-methoxy-2-(methylthio) pyrimidine, $^1$HNMR 8.19 (2H,m), 7.65 (3H,m), 7.25 (1H,dd,J=8,10 Hz), 6.45 (1H,s), 3.98 (3H,s), 2.55 (3H,s).

C. Similarly, replacing 4-chloro-6-isopropyl-2-(methylthio)pyrimidine with other compounds of formula (16) and following the procedures of Preparation 6A above, other compounds of formula (17) are prepared.

D. Alternative Preparation of (17) where $R^1$ is Lower Alkyl Substituted with Phenyl or Hydroxy, from Compounds of Formula (17) where $R^1$ is Alkyl A solution of 4-(4-fluoronaphth-2-yl)-6-methyl-2-(methylthio)-pyrimidine (0.500 g, 1.76 mmol) in tetrahydrofuran (2 mL) was added dropwise to a solution of lithium diisopropylamide (1.2 eq) in tetrahydrofuran (10 mL) cooled to –70° C. After stirring for 30 minutes, benzyl bromide (0.251 mL, 2.11 mmol) was added to the solution in one portion. The solution was warmed to room temperature and diuted with ethyl acetate (50 mL), poured into water (50 mL). The organic layer was separated, dried over magnesium sulfate and concentrated in vacuo, and the resultant oil purified by column chromatography to give 4-(4-fluoronaphth-1-yl)-2-methylthio-6-phenethylpyrimidine (0.342 g, 52%).

E. Similarly, replacing 4-(4-fluoronaphth-2-yl)-6-methyl-2-(methylthio)pyrimidine with other compounds of formula (16) where $R^1$ is alkyl and following the procedures of Preparation 6D above, the following compounds of formula (17) were prepared:
4-(4-fluoronaphth-1-yl)-6-(2-hydroxyphenethyl)-2-(methylthio)pyrimidine; and
4-(4-fluoronaphth-1-yl)-6-(3-hydroxypropyl)-2-(methylthio)pyrimidine.

F. Similarly, replacing 4-(4-fluoronaphth-2-yl)-6-methyl-2-(methylthio)pyrimidine with other compounds of formula (16) and following the procedures of Preparation 6C above, where $R^1$ is lower alkyl, other compounds of formula (17) are prepared.

PREPARATION 7

Preparation of Compounds of Formula (18)

A. Preparation of (18) where $R^1$ is Isopropyl, $R^4$-Fluoro-1-naphthyl 4-(4-Fluoronaphth-1-yl)-2-methylthio-6-phenethylpyrimidine (0.342 g, 0.914 mmol) was dissolved in methylene chloride at room temperature. meta-Chloroperoxybenzoic acid (55–60%, 0.554 g, 1.83 mmol) was added in small portions. After 16 hours, the reaction mixture was washed with saturated aqueous sodium bisulfite. The organic layer was washed with saturated aqueous sodium bicarbonate and water, dried over magnesium sulfate, and concentrated in vacuo to give 4-(4-fluoronaphth-1-yl)-2-methanesulfonyl-6-phenethylpyrimidine (0.402 g, 97%) as an oil, $^1$HNMR 8.07

(1H,m), 7.85 (1H,m), 7.47 (2H,m), 7.32 (1H,s), 7.13 (7H, m), 3.29 (2H,m), 3.07 (2H,m).

B. Similarly, replacing 4-(4-fluoronaphth-1-yl)-2-methylthio-6-phenethylpyrimidine with other compounds of formula (17), and following the procedure of Preparation 7A above, the following compounds of formula (18) were prepared:

4-(4-fluoronaphth-1-yl)-6-(2-hydroxyphenethyl)-2-methanesulfonyl-pyrimidine, m.p. 88.1–90.0° C.;

4-(4-fluoronaphth-1-yl)-6-(3-hydroxypropyl)-2-methanesulfonyl-pyrimidine, $^1$HNMR 8.21 (2H,m), 7.69 (1H,dd,J=5.3,8.2 Hz), 7.68 (1H,s), 7.61 (2H,m), 7.24 (1H,dd,J=8,10 Hz), 3.76 (2H,t,J=7.5 Hz), 3.40 (3H,s), 3.09 (2H,t,J=7.5 Hz), 2.11 (2H,m);

4-(4-fluoronaphth-1-yl)-6-methoxy-2-methanesulfonylpyrimidine, $^1$HNMR 8.20 (2H,m), 7.64 (3H,m), 7.25 (1H,dd,J=8,10 Hz), 7.15 (1H,s), 4.20 (3H,s), 3.39 (3H,s); and 4-(4-fluoronaphth-1-yl)-6-isopropyl-2-methanesulfonyl-pyrimidine, m.p. 96.1–97.1° C.

C. Similarly, replacing 4-(4-fluoronaphth-1-yl)-2-methylthio-6-phenethylpyrimidine with other compounds of formula (17), and following the procedure of Preparation 7A above, other compounds of formula (18) are prepared.

EXAMPLE 1

Preparation of a Compound of Formula I

A. Preparation of I where $R^1$ and $R^2$ are Methyl, $R^3$ is Naphth-1-yl, and $R^4$ and $R^5$ are Hydrogen A stirred heterogeneous solution of 1-naphthyl boronic acid (0.382 g), 2-amino-4-chloro-5,6-dimethylpyrimidine (0.350 g), tetrakis(triphenylphosphine)palladium(0) (0.153 g), ethyl alcohol (8 mL), water (4 mL), 1,2-dimethoxyethane (8 mL) and sodium carbonate (0.85 g), was heated to reflux (about 80° to 90° C.) for 14 hours. The solution was then cooled to room temperature, filtered and extracted with ethyl acetate. The solvent was removed under reduced pressure and the resultant yellow solid was recrystallized to give 2-amino-5,6-dimethyl-4-(naphth-1-yl)-pyrimidine (0.213 g), m.p. 213.5–215.1° C.

B. Similarly, optionally replacing 2-amino-4-chloro-5,6-dimethylpyrimidine with other compounds of formula (4), and optionally replacing 1-naphthyl boronic acid with other compounds of formula (5), and following the procedures of Example 1A above, the following compounds of Formula I were prepared:

2-amino-6-cyclopentyl-4-(naphth-1-yl)-pyrimidine, m.p. 146.8–147.4° C.;

2-amino-6-(but-2-yl)-4-(naphth-1-yl)-pyrimidine, m.p. 109.6–110.8° C.;

2-amino-6-(2-methylpropyl)-4-(naphth-1-yl)-pyrimidine hydrobromide, m.p. 147.0–151.5° C.;

2-amino-6-(tert-butyl)-4-(naphth-1-yl)-pyrimidine, m.p. 161.0–161.3° C.;

2-amino-6-benzyl-4-(naphth-1-yl)-pyrimidine, m.p. 147.9–148.2° C.;

2-amino-6-cyclobutyl-4-(naphth-1-yl)-pyrimidine, m.p. 147–148° C.;

2-amino-6-cyclopropyl-4-(naphth-1-yl)-pyrimidine, m.p. 182.8–184.0° C.;

2-amino-4-(naphth-1-yl)-6-n-propylpyrimidine, m.p. 119.5–120.5° C.;

2-amino-6-isopropyl-4-(naphth-1-yl)-pyrimidine, m.p. 124–126° C.;

2-amino-5-fluoro-6-methyl-4-(naphth-1-yl)-pyrimidine, m.p. 155–157° C.;

2-amino-6-ethyl-4-(naphth-1-yl)-pyrimidine hydrochloride, m.p. 157–160° C.;

2,6-diamino-4-(naphth-1-yl)-pyrimidine hydrochloride, m.p. >290° C.;

2-amino-6-trifluoromethyl-4-(naphth-1-yl)-pyrimidine, m.p. 152–154° C.;

2-amino-4-(naphth-1-yl)-6-phenylpyrimidine hydrochloride, m.p. 232–236° C.;

2-amino-4-(3-fluorophenyl)-6-methylpyrimidine, m.p. 140.6–141.4° C.;

2-amino-4-(5-chlorothiophen-2-yl)-6-methylpyrimidine, m.p. 186.1–187.3° C.;

2-amino-4-(3-methoxyphenyl)-6-methylpyrimidine, m.p. 125.8–129.6° C.;

2-amino-6-methyl-4-(3-nitrophenyl)-pyrimidine, m.p. 198.5–199.6° C.;

2-amino-4-(3-chloro-4-fluorophenyl)-6-methylpyrimidine, m.p. 163.8–165.5° C.;

2-amino-4-(3,5-dichlorophenyl)-6-methylpyrimidine, m.p. 187.0–187.9° C.;

2-amino-6-methyl-4-(3-trifluoromethylphenyl)-pyrimidine, m.p. 122.0–122.8° C.;

2-amino-6-methyl-4-(naphth-1-yl)-pyrimidine hydrochloride, m.p. 226° C.;

2-amino-4-(4-amino-5-chloro-2-methoxyphenyl)-6-isopropylpyrimidine hydrochloride, m.p. 187.1–190.6° C.;

2-amino-6-(3-methylbutyl)-4-(naphth-1-yl)-pyrimidine hydrochloride, m.p. 151.5–153° C.; and 2-amino-4-(4-amino-5-chloro-2-methoxyphenyl)-6-methylpyrimidine, m.p. 183–184° C.

C. Similarly, optionally replacing 2-amino-4-chloro-5,6-dimethylpyrimidine with other compounds of formula (4), and optionally replacing 1-naphthyl boronic acid with other compounds of formula (5), and following the procedures of Example 1A above, other compounds of Formula I are prepared.

EXAMPLE 2

Alternative Preparation of a Compound of Formula I

A. Preparation of I where $R^1$ is n-Propyl, $R^2$ is Hydrogen, $R^3$ is 4-Fluoronaphth-1-yl, and $R^4$ and $R^5$ are Hydrogen To a stirred solution of 1-bromo-4-fluoronaphthalene (0.5 g) in 10 mL of tetrahydrofuran at −78° C. under nitrogen was added n-butyllithium (1.6M, 1.53 mL) dropwise. The solution was allowed to stir for 5 minutes, then trimethoxyborane (0.33 mL) was added dropwise. The solution was allowed to warm to room temperature and the solvent removed under reduced pressure to give a solid, dimethoxy-(4-fluoronaphth-1-yl)borane, a compound of formula (7).

The solid was dissolved in 5 mL of benzene, and 2-amino-4-chloro-6-n-propylpyrimidine (0.381 g), tetrakis (triphenylphosphine)palladium(0) (0.100 g) and 6 mL of 2M aqueous sodium carbonate were added. The heterogeneous solution was heated to reflux (about 80° to 90° C.) for 1 hour, then the solution cooled to room temperature, diluted with ethyl acetate and filtered. The filtrate was concentrated in vacuo and the residue chromatographed on silica gel, eluting with a mixture of hexanes/ethyl acetate, to give 2-amino-4-(4-fluoronaphth-1-yl)-6-n-propylpyrimidine (0.110 g), m.p. 136.9–137.4° C.

B. Similarly, optionally replacing 1-bromo-4-fluoronaphthalene with other compounds of formula (6), and optionally replacing 2-amino-4-chloro-6-n- propylpyrimidine with other compounds of formula (4), and following the procedures of Example 2A above, the following compounds of Formula I were prepared:

2-amino-4-(4-chloronaphth-1-yl)-6-(2-methylpropyl)-pyrimidine hydrochloride, m.p. 198.2–199.8° C.;
2-amino-4-(4-fluoronaphth-1-yl)-6-(2-methylpropyl)-pyrimidine hydrochloride, m.p. 191.3–193.0° C.;
2-amino-4-(4-chloronaphth-1-yl)-6-ethylpyrimidine, m.p. 142.7–143.2° C.;
2-amino-4-(4-methylnaphth-1-yl)-6-isopropylpyrimidine, m.p. 143.9–145.0° C.;
2-amino-6-(tert-butyl)-4-(4-fluoronaphth-1-yl)-pyrimidine hydrochloride, m.p. 193–194° C.;
2-amino-4-(4,5-dimethylnaphth-1-yl)-6-methylpyrimidine, m.p. 194–195° C.;
2-amino-4-(4,5-difluoronaphth-1-yl)-6-isopropylpyrimidine, m.p. 123–124° C.;
2-amino-4-(4-chloronaphth-1-yl)-6-isopropylpyrimidine hydrochloride, m.p. 183.2–185.6° C.;
2-amino-6-cyclopropyl-4-(4-fluoronaphth-1-yl)-pyrimidine, m.p. 150.7–151.5° C.;
2-amino-6-cyclopropylmethyl-4-(4-fluoronaphth-1-yl)-pyrimidine hydrochloride, m.p. 128.4–129.4° C.;
2-amino-6-cyclobutyl-4-(4-fluoronaphth-1-yl)-pyrimidine hydrochloride, m.p. 168–171° C.;
2-amino-4-(4,5-difluoronaphth-1-yl)-6-methylpyrimidine, m.p. 200° C.;
2-amino-4-(1H,3H-benzo[de]isochromen-6-yl)-6-methylpyrimidine, m.p. 216–218° C.;
4-(acenaphthen-5-yl)-2-amino-6-isopropylpyrimidine, m.p. 167–168° C.;
2-amino-6-methyl-4-(phenanthren-9-yl)-pyrimidine, m.p. 191.3–191.8° C.;
2-amino-4-(4-methylnaphth-1-yl)-6-methylpyrimidine, m.p. 175.2–176.6° C.;
2-amino-4-(4-fluoronaphth-1-yl)-6-isopropylpyrimidine hydrochloride, m.p. 156–158° C.;
2-amino-4-(4-fluoronaphth-1-yl)-6-isopropylpyrimidine maleate, m.p. 155–157° C.;
2-amino-6-ethyl-4-(2-methyl-4-fluoronaphth-1-yl)-pyrimidine, m.p. 121–122° C.;
4-(acenaphthen-5-yl)-2-amino-6-methylpyrimidine, m.p. 211–213° C.;
2-amino-4-(isoquinolin-4-yl)-6-methylpyrimidine, m.p. 212.0–213.5° C.;
2-amino-6-methyl-4-(quinolin-8-yl)-pyrimidine, m.p. 194.8–195.5° C.;
2-amino-4-(4-fluoronaphth-1-yl)-pyrimidine, m.p. 203.4–204.1° C.;
2-amino-6-ethyl-4-(4-fluoronaphth-1-yl)-pyrimidine hydrochloride, m.p. 198–199° C.;
2-amino-4-(4-fluoronaphth-1-yl)-6-methylpyrimidine hydrochloride, m.p. 238.3–238.6° C.;
2-amino-4-(2-methylnaphth-1-yl)-6-methylpyrimidine hydrochloride, m.p. 216.6–219.4° C.;
2-amino-4-(4-fluoronaphth-1-yl)-6-(3,3,3-trifluoropropyl)-pyrimidine hydrochloride, m.p. 152–155° C.;
2-amino-4-(5-fluoronaphth-1-yl)-6-isopropylpyrimidine, m.p. 86–88° C.;
2-amino-4-(2-fluoronaphth-1-yl)-6-isopropylpyrimidine hydrochloride, m.p. 205–206° C.;
2-amino-4-(2-fluoronaphth-1-yl)-6-methoxypyrimidine hydrochloride, m.p. 189–190° C.;
2-amino-4-(4-fluoronaphth-1-yl)-6-methoxypyrimidine hydrochloride, m.p. >280° C.;
2-amino-4-(4-fluoronaphth-1-yl)-6-(2,2,2-trifluoroethoxy)-pyrimidine hydrochloride, m.p. 206.1–208° C.;
2-amino-6-tert-butyl-4-(2-fluoronaphth-1-yl)-pyrimidine hydrochloride, m.p. 230–233° C.;
2-amino-4-(2-fluoronaphth-1-yl)-6-methylpyrimidine, m.p. 149–150° C.;
2-amino-6-isopropyl-4-(2-methylnaphth-1-yl)-pyrimidine hydrochloride, m.p. 193–194° C.;
2-amino-4-(6-methylacenaphthen-5-yl)-6-methylpyrimidine, m.p. 198–199° C.;
2-amino-6-cyclopropyl-4-(1H-indol-4-yl)-pyrimidine hydrochloride, m.p. >280° C.;
2-amino-6-tert-butyl-4-(1H-indol-4-yl)-pyrimidine, m.p. 171–173° C.;
2-amino-4-(8-hydroxymethylnaphth-1-yl)-6-methylpyrimidine, m.p. 206–208° C.;
2-amino-4-(1H-indol-7-yl)-6-isopropylpyrimidine, m.p. 143–145° C.;
2-amino-6-cyclobutyl-4-(1H-indol-4-yl)-pyrimidine, m.p. 225–226° C.;
4-(acenaphthen-5-yl)-2-amino-6-methoxypyrimidine hydrochloride, m.p. 205.0–208.0° C.;
4-(acenaphthen-5-yl)-2-amino-6-cyclopropylpyrimidine, m.p. 210.0–211.5° C.; and
4-(acenaphthen-5-yl)-2-amino-6-tert-butylpyrimidine hydrochloride, m.p. 263.4–265.6° C.

C. Similarly, optionally replacing 1-bromo-4-fluoronaphthalene with other compounds of formula (6), and optionally replacing 2-amino-4-chloro-6-n-propylpyrimidine with other compounds of formula (4), and following the procedures of Example 2A above, other compounds of Formula I are prepared.

EXAMPLE 3

Alternative Preparation of a Compound of Formula I

A. Preparation of I where $R^1$ is Methyl, $R^2$ is Hydrogen, $R^3$ is 6-Methoxy-3,4-Dihydro-2H-Quinolin-1-yl, and $R^4$ and $R^5$ are Hydrogen A flask containing 6-methoxy-1,2,3,4-tetrahydroquinoline (1.33 g), 2-amino-4-chloro-6-methylpyrimidine (1.00 g), sulfuric acid (0.6 g), and 100 mL of water was heated on a steam bath for 2 hours. The solution was then cooled to room temperature and treated with ammonium hydroxide until the solution was basic (pH 8–9). The resultant solid, which precipitated from solution, was collected by filtration and recrystallized from ethyl alcohol to give 2-amino-4-(6-methoxy-3,4,-dihydro-2H-quinolin-1-yl)-6-methylpyrimidine (0.93 g), m.p. 175.2–175.9° C.

B. Similarly, optionally replacing 6-methoxy-1,2,3,4-tetrahydroquinoline with other compounds of formula (8), and optionally replacing 2-amino-4-chloro-6-methylpyrimidine with other compounds of formula (4), and following the procedures of Example 3A above, the following compounds of Formula I were prepared:
2-amino-4-(6-fluoro-3,4-dihydro-2H-quinolin-1-yl)-6-methylpyrimidine, m.p. 156–157° C.;
2-amino-6-chloro-4-(3,4-dihydro-2H-quinolin-1-yl)-pyrimidine hydrochloride, m.p. >180° C. (dec);
2-amino-4-(indol-1-yl)-6-methylpyrimidine hydrochloride, m.p. 256–260° C.;
2,6-diamino-4-(3,4-dihydro-2H-quinolin-1-yl)-pyrimidine dihydrochloride, m.p. 196–197° C.;
6-(3,4-dihydro-2H-quinolin-1-yl)-9H-purin-2-ylamine, m.p. 203.5–204.0° C.;
2-amino-4-(2-methyl-3,4-dihydro-2H-quinolin-1-yl)-6-methylpyrimidine, m.p. 141–144° C.;

2-amino-4-(6-methoxy-3,4-dihydro-2H-quinolin-1-yl)-6-trifluoromethylpyrimidine, m.p. 175.6–177.5° C.;

2-amino-4-(3,4-dihydro-2H-quinolin-1-yl)-6-ethylpyrimidine, m.p. 141.4–142.1° C.;

2-amino-6-methyl-4-(6-methyl-3,4-dihydro-2H-quinolin-1-yl)-pyrimidine, m.p. 170.6–171.4° C.;

2-amino-4-(3,4-dihydro-2H-quinolin-1-yl)-6-trifluoromethylpyrimidine, m.p. 162–164° C.;

2-amino-4-(6-fluoro-2-methyl-3,4-dihydro-2H-quinolin-1-yl)-6-methylpyrimidine, m.p. 154.9–155.6° C.;

2-amino-6-methyl-4-(2,3,4,5-tetrahydro-benzo[b]azepin-1-yl)-pyrimidine, m.p. 182.6–184.2° C.;

2-amino-4-(7,8-dihydro-6H-5-oxa-9-benzocyclohepten-9-yl)-6-methylpyrimidine, m.p. 189.9–192.0° C.;

2-amino-4-(2,3-dihydro-benzo[1,4]oxazin-4-yl)-6-methylpyrimidine, m.p. 177.7–178.5° C.;

2-amino-4-(2,3-dihydro-indol-1-yl)-6-methylpyrimidine, m.p. 247.7–248.0° C.;

2-amino-4-(2-methyl-2,3-dihydro-indol-1-yl)-6-methylpyrimidine, m.p. 182.9–183.4° C.;

2-amino-4-(3,4-dihydro-2H-quinolin-1-yl)-6-methylpyrimidine hydrochloride, m.p. 261.5–262.3° C.;

2-amino-4-(3,4-dihydro-1H-isoquinolin-2-yl)-6-methylpyrimidine, m.p. 142.2–143.3° C.;

2-amino-4-(3,4-dihydro-2H-quinolin-1-yl)-6-isopropylpyrimidine hydrochloride, m.p. 210.6–211.1° C.;

2-amino-4-(6-fluoro-3,4-dihydro-2H-quinolin-1-yl)-6-isopropylpyrimidine hydrochloride, m.p. 255.5–257.5° C.; and 2-amino-4-(3,4-dihydro-2H-quinolin-1-yl)-6-tert-butylpyrimidine hydrochloride, m.p. 263.6–265.0° C.

C. Preparation of I where $R^1$ is Chloro, $R^2$ is Hydrogen, $R^1$ is 3,4-Dihydro-2H-Quinolin-1-yl, and $R^4$ and $R^5$ are Hydrogen 1,2,3,4,-tetrahydroquinoline (2.66 g, 20 mmol) and 2-amino-4,6-dichloropyrimidine (3.30 g, 20 mmol) were dissolved in 10 mL of N,N-dimethylformamide (DMF), and the entire solution was heated to 70–90° C. for 24 hours. DMF was removed under vacuum, and the residue was refluxed with ethyl acetate to give 4.0 g of a solid; the solid was chromatographed on silica gel, eluting with methylene chloride, to give 2-amino-6-chloro-4-(3,4-dihydro-2H-quinolin-1-yl)-pyrimidine (400 mg), m.p. 167.1–167.5° C.; 2-amino-6-chloro-4-(3,4-dihydro-2H-quinolin-1-yl)-pyrimidine hydrochloride, m.p. 179° C. (dec.).

D. Similarly, optionally replacing 6-methoxy-1,2,3,4-tetrahydroquinoline with other compounds of formula (8), and optionally replacing 2-amino-4-chloro-6-methylpyrimidine with other compounds of formula (4), and following the procedures of Example 3A or 3C above, other compounds of Formula I are prepared.

EXAMPLE 4

Alternative Preparation of a Compound of Formula I

A. Preparation of I where $R^1$ is N,N-diethylamino, $R^2$ is Hydrogen, $R^3$ is 3,4-Dihydro-2H-Quinolin-1-yl, and $R^4$ and $R^5$ are Hydrogen Excess diethylamine was added to a solution of 2-amino-6-chloro-4-(1,2,3,4-tetrahydroquinolin-1-yl)-pyrimidine (250 mg) in 5 mL of ethylene glycol. The mixture was heated for 2 days at 100° C. The crude product was purified by chromatography to give 300 mg of a solid. Treatment of the solid with hydrochloric acid-ethanol alcohol yielded 2-amino-6-diethylamino-4-(3,4-dihydro-2H-quinolin-1-yl)-pyrimidine hydrochloride, m.p. 167–170° C.

B. Similarly, optionally replacing diethylamine with other amines of formula $HNR^6R^7$, and optionally replacing 2-amino-6-chloro-4-(1,2,3,4-tetrahydroquinolin-1-yl)-pyrimidine with other compounds of Formula I where $R^1$ is chloro, and following the procedures of Example 4A above, other compounds of Formula I where $R^1$ is —$NR^6R^7$ are prepared.

EXAMPLE 5

Alternative Preparation of a Compound of Formula I

A. Preparation of I where $R^1$ is Methyl, $R^2$ is Hydrogen, $R^3$ is 1H-Indol-4-yl, and $R^4$ and $R^5$ are Hydrogen 4-Acetylindole (0.101 g) was refluxed in 5 mL of ethyl acetate. Sodium hydride (0.20 g, 60% oil dispersion) was added in portions to the refluxing solution until thin layer chromatography analysis showed complete consumption of the starting material. The reaction mixture was quenched with water and acidified to pH 3. The ethyl acetate layer was dried (magnesium sulfate) and concentrated to give a crude product. The crude material was chromatographed on silica gel, eluting with hexane/ethyl acetate to give 1-(1H-indol-4-yl)-1,3-butanedione (0.104 g), a compound of formula (11), m.p. 104–105° C.

B. 1-(1H-Indol-4-yl)-1,3-butanedione (0.096 g) was mixed with guanidine carbonate (0.070 g), and the mixture was heated to 150° C. for 3 hours. Additional guanidine carbonate (0.070 g) was added, and the mixture continued to heat for another 2 hours. The reaction mixture was warmed with ethyl acetate, filtered, and the ethyl acetate layer was concentrated to give a solid (0.090 g). Flash chromatography on silica gel, eluting with hexane/ethyl acetate, yielded 2-amino-4-(1H-indol-4-yl)-6-methylpyrimidine (0.029 g), m.p. 242–243.5° C.

C. Similarly, replacing 4-acetylindole with 1-acetylnaphthalene in step 5A above, and replacing guanidine carbonate with 1-arginine in step B, and following the procedures of Example 5A and 5B, the compound 2-amino-5-(6-methyl-4-naphth-1-yl)-pyrimidin-2-ylamino)-pentanoic acid, m.p. 264–266° C. was prepared.

D. Similarly, replacing 4-acetylindole with ethyl(1-naphthoyl)acetate in step 5A, and following the procedures of Example 5A and 5B, the compound 2-amino-6-methyl-4-(naphth-1-yl)-pyrimidine hydrochloride, m.p. 270–272° C. was prepared.

E. Similarly, replacing 1-(1H-indol-4-yl)-1,3-butanedione with 1-(3-chlorophenyl)-1,3-butanedione and following the procedures of Example 5B above, the compound 2-amino-4-(3-chlorophenyl)-6-methylpyrimidine, m.p. 131.6–132.3° C. was prepared.

F. Preparation of I where $R^1$ is Methyl, $R^2$ is Hydrogen, $R^3$ is 2,3-dihydro-1,4-benzodioxin-5-yl, and $R^4$ and $R^5$ are Hydrogen 1-(2,3-Dihydro-1,4-benzodioxin-5-yl)-ethanone (1.2 g) was dissolved in 20 mL of ethyl acetate, and sodium hydride (0.33 g, 60% oil dispersion) was added. The reaction mixture was heated to 80° C. overnight, quenched with water, and neutralized with carbon dioxide to give an oily product of 1-(2,3-dihydro-1,4-benzodioxin-5-yl)butan-1,3-dione (0.37 g).

The 1-(2,3-dihydro-1,4-benzodioxin-5-yl)-butan-1,3-dione (0.37 g), was mixed with guanidine carbonate (0.22 g), and the mixture was heated to 135° C. for 1 hour. The dark product was taken up in methylene chloride, filtered, and concentrated. The residue was chromatographed on silica gel, eluting with ethyl acetate/hexane, to give a solid (0.16 g), which was treated with hydrochloric acid-ethanol to give 2-amino-4-(2,3-dihydro-1,4-benzodioxin-5-yl)-6-methylpyrimidine hydrochloride (0.125 g), m.p. 240–242° C.

G. Preparation of I where $R^1$ and $R^2$ are Hydrogen, $R^3$ is 1-methylindol-3-yl, and $R^4$ and $R^5$ are Hydrogen 3-Acetyl-1-methylindole (0.870 g) was dissolved in 3 mL of absolute ethanol. Tert-butoxybis(dimethylamino)methane (Bredereck's reagent) (0.960 g) in 3 mL of ethanol was added to this solution at reflux temperature. The solution was refluxed for 2 days and the solvent was removed at room temperature under vacuum. The residue was triturated with hexane/ethyl acetate to give a solid (0.094 g).

The solid was mixed with guanidine carbonate (0.037 g) and the mixture was heated to 120° C. for 14 hours. The reaction mixture was dissolved in hot absolute ethyl alcohol, filtered, and recrystallized to give a white, crystalline solid of 2-amino-4-(1-methylindol-3-yl)-pyrimidine (0.039 g). Treatment of the crystalline solid with hydrochloric acid-ethyl alcohol and recrystallization of the salt from ethanol gave 2-amino-4-(1-methylindol-3-yl)-pyrimidine hydrochloride (0.0098 g), m.p. 274–276° C.

H. Preparation of I where $R^1$ is Isopropyl, $R^2$ is Hydrogen, $R^3$ is 4,7-difluoronaphth-1-yl, and $R^4$ and $R^5$ are Hydrogen 1-(4,7-difluoronaphth-1-yl)-ethanone (0.150 g, 0.72 mmol) was dissolved in dry dioxane (1 mL) and cooled to 0° C. Sodium hydride (0.145 g, 3.6 mmol, 60 wt. % dispersion) was added and the reaction mixture was stirred for 1 hour at room temperature. Ethyl isobutyrate (1.0 mL, 7.2 mmol) was added in one portion and the solution was heated to reflux for 15 minutes. After cooling to room temperature, the reaction mixture was poured onto 10% aqueous hydrochloric acid and extracted with methylene chloride. The organic layer was dried over sodium sulfate and purified by column chromatography to give 1-(4,7-difluoronaphth-1-yl)-4-methylpentane-1,3-dione (0.120 g, 72%).

I. 1-(4,7-difluoronaphth-1-yl)-4-methylpentane-1,3-dione (0.114 g, 0.5 mmol) was combined with guanidine carbonate (0.180 g, 0.5 mmol) and heated to 150° C. for 6 hours. The reaction was cooled to room temperature and directly purified by column chromatography to give 2-amino-4-(4,7-difluoronaphth-1-yl)-6-isopropylpyrimidine (0.052 g, 34%), m.p. 103–105° C.

J. Similarly, replacing 1-(4,7-difluoronaphth-1-yl)-ethanone with 1-(4,6-difluoronaphth-1-yl)-ethanone, 1-(4,8-difluoronaphth-1-yl)-ethanone, 1-(4-methoxynaphth-1-yl)-ethanone, or 1-(l-methyl-1H-indol-4-yl)-ethanone in step 5H, and optionally replacing ethyl isobutyrate with 4,4-dimethyl-3-oxopentanoate or 4,4-dimethyl-3-oxopentanoate, or ethyl-2-fluoroisobutyrate, and guanidine with substituted guanidine salts in step 5I, and following the procedures of Example 5H and 5I, the following compounds were prepared:

2-amino-4-(4,6-difluoronaphth-1-yl)-6-isopropylpyrimidine hydrochloride, m.p. 136–138° C.;
2-amino-4-(4,8-difluoronaphth-1-yl)-6-isopropylpyrimidine hydrochloride, m.p. 216–219° C.;
2-amino-4-(4-methoxynaphth-1-yl)-6-isopropylpyrimidine hydrochloride, m.p. 196–197° C.;
2-amino-6-tert-butyl-4-(4-methoxynaphth-1-yl)-pyrimidine hydrochloride, m.p. 219–220.5° C.;
2-amino-4-(1H-indol-4-yl)-6-isopropylpyrimidine hydrochloride, m.p. 211–212° C.;
2-amino-4-(1-methyl-1H-indol-4-yl)-6-isopropylpyrimidine, m.p. 128–130° C.;
2-amino-4-(4-fluoronaphth-1-yl)-6-(1-fluoro-1-methylethyl)-pyrimidine, m.p. 135.5–137.0° C.;
2-amino-4-(4-fluoronaphth-1-yl)-6-(1-fluoro-1-methylethyl)-pyrimidine hydrochloride, m.p. 186.6–187.8° C.;
4-(4-fluoronaphth-1-yl)-6-(1-fluoro-1-methylethyl)-2-methylaminopyrimidine, m.p. 149–151° C.;
2-amino-4-(4-methoxynaphth-1-yl)-6-methylpyrimidine hydrochloride, m.p. 247.0–249.5° C.;
2-amino-6-ethyl-4-(4-methoxynaphth-1-yl)-pyrimidine hydrochloride, m.p. 218.5–218.9° C.;
2-amino-4-(4,6-difluoronaphth-1-yl)-6-(1-fluoro-1-methylethyl)-pyrimidine hydrochloride, m.p. 129.6–131.3° C.; and
2-amino-4-(acenaphthen-5-yl)-6-(1-methyl-1-fluoroethyl)-pyrimidine, m.p. 170.5–172.4° C.

EXAMPLE 6

Alternative Preparation of a Compound of Formula I

A. Preparation of I where $R^1$ is Chloro, $R^2$ is Hydrogen, $R^3$ is Naphth-1-yl, and $R^4$ and $R^5$ are Hydrogen 2-Amino-6-hydroxy-4-(naphth-1-yl)-pyrimidine (900 mg) was added to a solution of chlorosulfonic acid (0.05 mL) in 2.5 mL of phosphorus oxychloride, and the mixture was stirred at 95° C. for 6 hours. The mixture was poured onto ice, neutralized with potassium carbonate, and extracted with ethyl acetate. The crude product (70 mg) was purified by silica gel chromatography, eluting with methylene chloride, and treated with hydrochloric acid-ethanol to give 2-amino-6-chloro-4-(naphth-1-yl)-pyrimidine hydrochloride (25 mg), m.p. 248–250° C.

B. Preparation of I where $R^1$ and $R^2$ are Hydrogen, $R^3$ is Naphth-1-yl, and $R^4$ and $R^5$ are Hydrogen 2-Amino-6-chloro-4-(naphth-1-yl)-pyrimidine (170 mg) was dissolved in 10 mL of methyl alcohol at 0° C. 10% Palladium on activated carbon (70 mg) and approximately 1 mL of 20% sodium hydroxide were added to the solution, and the mixture was hydrogenated (1 atmosphere) for 1 hour to give solid 2-amino-4-(naphth-1-yl)-pyrimidine (80 mg). Treatment of the solid with hydrochloric acid/ethyl alcohol yielded 2-amino-4-(naphth-1-yl)-pyrimidine hydrochloride (25 mg), m.p. 181–184° C.

EXAMPLE 7

Alternative Preparation of a Compound of Formula I

A. Preparation of I where $R^1$ is Methoxy, $R^2$ is Hydrogen, $R^3$ is Naphth-1-yl, and $R^4$ and $R^5$ are Hydrogen 1-Acetonaphthalene (33 g) in carbon disulfide (15 g) was added over 15 minutes to a 12° C. solution containing 195 mL of 1M potassium tert-butoxide in 400 mL of ether. The reaction mixture was allowed to warm to room temperature, re-cooled to 10–12° C., and then methyl iodide (55.0 g) was added dropwise over 45 minutes. The reaction mixture was brought to room temperature for 16 hours, filtered, and concentrated. The residue was recrystallized from methyl alcohol to give 3,3-(bis-methylsulfanyl)-(1-naphth-1-yl)-prop-2-en-1-one (20.1 g), m.p. 73–79° C.

B. The 3,3-(bis-methylsulfanyl)-(1-naphthalen-1-yl)prop-2-en-1-one (1.28 g) was added to 10 mL of a methanolic solution of sodium hydride (640 mg, 60% oil dispersion) and guanidine carbonate (630 g). The reaction mixture was refluxed for 6 hours, poured into ethyl acetate, and washed with saturated sodium bicarbonate, water, and brine. The organic layer was dried over potassium carbonate and concentrated to about 5 mL to give a crystalline solid of 2-amino-6-methoxy-4-(naphth-1-yl)-pyrimidine, m.p. 159.6–159.8° C. Treatment of the crystalline solid with hydrochloric acid/ethyl alcohol gave 2-amino-4-methoxy-6-(naphth-1-yl)-pyrimidine hydrochloride (300 mg), m.p. 184–185° C.

C. Similarly, replacing the methanolic solution with the corresponding alcohol (ethylene glycol, isopropyl alcohol, ethyl alcohol) and following the procedures of Example 7B above, the following compounds of Formula I were prepared:

2-amino-6-(2-hydroxyethoxy)-4-(naphth-1-yl)-pyrimidine hydrochloride, m.p. 199–201° C.;
2-amino-6-isopropyloxy-4-(naphth-1-yl)-pyrimidine hydrochloride, m.p. 165–167° C.; and
2-amino-6-ethoxy-4-(naphth-1-yl)-pyrimidine hydrochloride, m.p. 194–195° C.

D. Preparation of I where $R^1$ is Methylthio. $R^2$ is Hydrogen, $R^3$ is Naphth-1-yl, and $R^4$ and $R^5$ are Hydrogen The 3,3-(bis-methylsulfanyl)-(1-naphth-1-yl)-prop-2-en-1-one (1.13 g) was added to a mixture of sodium hydride (0.38 g, 60% oil dispersion) and guanidine carbonate (0.40 g) in 10 mL of N,N-dimethylformamide (DMF) at room temperature. After 1 hour, the mixture was heated to 150° C. for 5 hours. Extractive work-up gave a crude product which was chromatographed on silica gel, eluting with hexane/ethyl acetate to give 2-amino-4-methylthio-6-(1-naphthyl)-pyrimidine (140 mg). Treatment of the free base with hydrochloric acid-ethyl alcohol gave 2-amino-6-methylthio-4-(naphth-1-yl)-pyrimidine hydrochloride (80 mg), m.p. 255–259° C. (dec.).

EXAMPLE 8

Alternative Preparation of a Compound of Formula I

A. Preparation of I where $R^1$ is Isopropyl, $R^2$ is Hydrogen, $R^3$ is Naphth-1-yl, $R^4$ is Ethyl and $R^5$ is Hydrogen 4-(4-fluoronaphth-1-yl)-6-isopropyl-2-methanesulfonylpyrimidine (0.100 g, 0.29 mmol) was added to a solution of ethylamine (0.33 mL, 5.8 mmol) in ethanol (1 mL). The reaction vessel was placed in a sonication bath for 6 hours at a bath temperature of 45° C. The ethanol was removed in vacuo leaving a viscous oil. The oil was crystallized from ethanol and water to give 2-ethylamino-4-(4-fluoronaphth-1-yl)-6-isopropylpyrimidine (49%), m.p. 77–78° C.

B. Similarly, replacing ethylamine with other amines of formula $NHR^4R^5$ and optionally replacing 4-(4-fluoronaphth-1-yl)-6-isopropyl-2-methanesulfonylpyrimidine with other compounds of formula (18), and following the procedures of Example 8A above, the following compounds of Formula I were prepared:

4-(4-fluoronaphth-1-yl)-2-hydrazino-6-isopropylpyrimidine hydrochloride, m.p. 141–145° C.;
4-(4-fluoronaphth-1-yl)-6-isopropyl-2-(piperazin-1-yl)-pyrimidine fumarate, m.p. 196.1–196.6° C.;
4-(4-fluoronaphth-1-yl)-6-isopropyl-2-(2-methoxyethylamino)-pyrimidine, m.p. 87.1–87.7° C.;
4-(4-fluoronaphth-1-yl)-6-isopropyl-2-n-propylamino-pyrimidine, m.p. 99.6–99.9° C.;
2-allylamino-4-(4-fluoronaphth-1-yl)-6-isopropylpyrimidine, m.p. 92.8–93.4° C.;
4-(4-fluoronaphth-1-yl)-6-isopropyl-2-(piperidin-1-yl)-pyrimidine, m.p. 70–72° C.;
2-benzylamino-4-(4-fluoronaphth-1-yl)-6-isopropylpyrimidine, m.p. 73–74° C.;
2-cyclopropylamino-4-(4-fluoronaphth-1-yl)-6-isopropylpyrimidine, m.p. 100.1–100.8° C.;
2-(2-hydroxyethylamino)-4-(4-fluoronaphth-1-yl)-6-isopropylpyrimidine hydrochloride, m.p. 70–71° C.;
4-(4-fluoronaphth-1-yl)-6-isopropyl-2-morpholinopyrimidine, m.p. 81–83° C.;
2-butylamino-4-(4-fluoronaphth-1-yl)-6-isopropylpyrimidine, m.p. 87–88° C.;
2-butylamino-4-(4-fluoronaphth-1-yl)-6-methylpyrimidine hydrochloride, m.p. 137–139° C.;
2-dimethylamino-4-(4-fluoronaphth-1-yl)-6-isopropylpyrimidine, m.p. 41–42° C.;
4-(4-fluoronaphth-1-yl)-6-isopropyl-2-methylaminopyrimidine, m.p. 115–116° C.;
4-(4-fluoronaphth-1-yl)-6-(2-hydroxy-2-phenethyl)-2-methylaminopyrimidine, m.p. 138.1–139.2° C.;
4-(4-fluoronaphth-1-yl)-6-phenethyl-2-methylaminopyrimidine hydrochloride, m.p. 130.7–131.2° C.;
4-(4-fluoronaphth-1-yl)-2-isopropylamino-6-methoxypyrimidine hydrochloride, m.p. 191.3–191.6° C.;
2-(dimethylaminoethyl)amino-4-(4-fluoronaphth-1-yl)-6-isopropypyrimidine hydrochloride, m.p. 176.5° C.;
4-(4-fluoronaphth-1-yl)-6-isopropy-2-(methylaminoethyl) amino-pyrimidine hydrochloride, m.p. 152–153° C.;
4-(4-fluoronaphth-1-yl)-6-(2-hydroxypropyl)-2-(methylamino)-ethylamino-pyrimidine hydrochloride, m.p. 125–130° C.;
2-(2-hydroxyethyl)amino-4-(4-fluoronaphth-1-yl)-6-methoxypyrimidine hydrochloride, m.p. 191.3–191.6° C.;
6-tert-butyl-4-(4-fluoronaphth-1-yl)-2-methylaminopyrimidine, m.p. 129.4–130.0° C.;
2-benzylamino-6-tert-butyl-4-(4-fluoronaphth-1-yl)-pyrimidine, m.p. 106.2–106.9° C.;
6-tert-butyl-4-(4-fluoronaphth-1-yl)-2-isopropylamino-pyrimidine hydrobromide, m.p. 196.5–197.2° C.;
6-tert-butyl-4-(4-fluoronaphth-1-yl)-2-(2-methoxyethyl) amino-pyrimidine hydrochloride, m.p. 114.5–117.80C;
4-(4-fluoronaphth-1-yl)-6-isopropyl-2-(pyridin-4-yl) methylamino-pyrimidine, m.p. 149.1–149.5° C.;
2-(2-amino)ethylamino-4-(4-fluoronaphth-1-yl)-6-isopropyl-pyrimidine fumarate, m.p. 172.4–172.6° C.;
4-(4-fluoronaphth-1-yl)-6-isopropyl-2-(4-methoxyphenyl) methylamino-pyrimidine hydrochloride, m.p. 65–67° C.;
4-(4-fluoronaphth-1-yl)-2-(tetrahydro-2-furyl) methylamino-6-isopropyl-pyrimidine sodium, m.p. 72.7–73.8° C.;
4-(4-fluoronaphth-1-yl)-2-(2-hydroxyethyl)amino-6-isopropyl-pyrimidine maleate, m.p. 101.9–104.1° C.;
4-(4-fluoronaphth-1-yl)-2-(2-hydroxyethoxyethyl)amino-6-isopropyl-pyrimidine hydrobromide, m.p. 115.3–116.7° C.;
2-(1,3-dihydroxyprop-2-yl)amino-4-(4-fluoronaphth-1-yl)-6-isopropyl-pyrimidine maleate, m.p. 125.3–126.6° C.;
2-amino-4-(4-fluoronaphth-1-yl)-6-(2-methoxyethyl) pyrimidine maleate, m.p. 94–100° C.;
2-amino-4-(4-fluoronaphth-1-yl)-6-phenethylpyrimidine maleate, m.p. 145–146° C.;
4-(4-fluoronaphth-1-yl)-2-(2-hydroxyethyl)amino-6-isopropylpyrimidine bromide, m.p. 115.3–116.7° C.; and
2-(2-aminoethyl)amino-6-tert-butyl-4-(4-fluoronaphth-1-yl)-pyrimidine fumarate, m.p. 163.0–163.5° C.

C. Similarly, optionally replacing ethylamine with other amines of formula NHR$^4$R$^5$ and optionally replacing 4-(4-fluoronaphth-1-yl)-6-isopropyl-2-methanesulfonylpyrimidine with other compounds of formula (18), and following the procedures of Example 8A above, other compounds of Formula I are prepared.

D. Alternative Preparation of I where R$^1$ is Isopropyl, R$^2$ is Hydrogen, R$^3$ is Naphth-1-yl, R$^4$ is Phenyl and R$^5$ is Hydrogen Compounds of Formula I are alternatively prepared by the treatment of 4-(4-fluoronaphth-1-yl)-6-isopropyl-2-methanesulfonylpyrimidine with aniline in the absence of solvent at a higher temperatures of 120° C. to afford 4-(4-fluoronaphth-1-yl)-6-isopropyl-2-phenylaminopyrimidine, m.p. 85.7–86.3° C.

EXAMPLE 9

Preparation of an N-oxide of a Compound of Formula I

A. Preparation of The N-Oxide of I where R$^1$ is Methyl, R$^2$ is Hydrogen, R$^3$ is Naphth-1-yl, and R$^4$ and R$^5$ are Hydrogen 2-Amino-6-methyl-4-(naphth-1-yl)-pyrimidine (0.28 g) was dissolved in 15 mL of chloroform at 0° C. m-Chloroperbenzoic acid (0.54 g) was added to the solution in portions over 5 minutes. After complete addition, the solution was warmed to 40° C. for 30 minutes. The solution was washed with 10% aqueous sodium thiosulfate, 1M sodium hydroxide, and water. The chloroform layer was dried (sodium sulfate) and concentrated; the solid residue was recrystallized from ethyl alcohol/diethyl ether to give 2-amino-6-methyl-4-(naphth-1-yl)-pyrimidine-1-N-oxide (0.07 g), m.p. 228.7–229.5° C.

B. Similarly, replacing 2-amino-6-methyl-6-(naphth-1-yl)-pyrimidine with other compounds of Formula I, and following the procedures of Example 9A above, the following N-oxides of compounds of Formula I were prepared:
2-amino-4-(4-fluoronaphth-1-yl)-6-isopropylpyrimidine-3-N-oxide, m.p. 188–189° C.;
2-amino-6-tert-butyl-4-(4-fluoronaphth-1-yl)-pyrimidine-3-N-oxide, m.p. 188.6–190.9° C.;
2-amino-4-(4-fluoronaphth-1-yl)-6-isopropylpyrimidine-1-N-oxide hydrochloride, m.p. 207–208° C.;
2,6-diamino-4-(naphth-1-yl)-pyrimidine-1-N-oxide, m.p. 254.1–255.5° C.;
2-amino-4-(4-fluoronaphth-1-yl)-6-isopropylpyrimidine-1-N-oxide, m.p. 153–155° C.;
2-amino-4-(4-fluoronaphth-1-yl)-6-isopropylpyrimidine-3-N-oxide, m.p. 188–189° C.;
4-(4-fluoronaphth-1-yl)-6-isopropylpyrimidine-2-methylamino-1-N-oxide, m.p. 181–182.5° C.; and
2-amino-4-(acenaphthen-5-yl)-6-isopropylpyrimidine-1-N-oxide, m.p. 193.3–194.2° C.

C. Similarly, replacing 2-amino-6-methyl-4-(naphth-1-yl)-pyrimidine with other compounds of Formula I and following the procedures of Example 9A above, other N-oxides of compounds of Formula I are prepared.

EXAMPLE 10

Preparation of a Compound of Formula I where R$^1$ is Hydroxyalkyl or Alkenyl

A. Preparation of I where R$^1$ is 1-Hydroxy-1-methylethyl or Isopropenyl, R$^2$ is Hydrogen, R$^3$ is Naphth-1-yl, and R$^4$ and R$^5$ are Hydrogen Trifluoroacetic anhydride (0.211 mL, 1.50 mmol) was added to a solution of 2-amino-4-(4-fluoronaphth-1-yl)-6-isopropylpyrimidine-3-N-oxide (0.148 g, 0.498 mmol) in methylene chloride (5 mL) at room temperature. The mixture was stirred for 48 hours at room temperature and then poured into 1N aqueous sodium hydroxide. The organic layer was removed, concentrated in vacuo, purified by preparative thin layer chromatography to give a mixture of 2-amino-4-(4-fluoronaphth-1-yl)-6-(1-hydroxy-1-methylethyl)-pyrimidine (0.043 g, 29%), m.p. 181–184° C.; and 2-amino-4-(4-fluoronaphth-1-yl)-6-isopropenylpyrimidine (0.051 g, 36%), m.p. 138–140° C.

B. Similarly, replacing 2-amino-4-(4-fluoronaphth-1-yl)-6-isopropylpyrimidine-3-N-oxide with other N-oxides of compounds of Formula I and following the procedures of Example 10A above, other compounds of Formula I where R$^1$ is hydroxyalkyl or alkenyl are prepared.

EXAMPLE 11

Conversion of Compounds of Formula I where R$^1$, R$^2$ and R$^3$ are as defined in the Summary of the Invention, and R$^4$ and R$^5$ are Hydrogen to Other Compounds of Formula I, varying R$^4$ and/or R$^5$ A. Preparation of I where R$^4$ is acetyl and R$^5$ is Hydrogen 2-Amino-4-(4-fluoronaphth-1-yl)-6-isopropylpyrimidine (0.5 g) was dissolved in acetic anhydride (10 mL) and 4-dimethylaminopyridine (0.125 g) was added. The reaction mixture was stirred overnight at room temperature, then heated at 75° to 80° C. for a total of 4 hours, and evaporated to dryness under vacuum. The residue was partitioned between water and ethyl acetate and then dried over magnesium sulfate. The diacetyl compound was isolated as an oil by evaporation and then dissolved in methanol (20 mL). The solution was treated with saturated sodium bicarbonate solution (2 mL) and allowed to stir overnight. The resulting monoacetyl derivative was isolated by evaporation to dryness and thorough drying under vacuum. The residue was taken up in boiling hexane and decanted from a small amount of insoluble residue and crystallized to yield 2-acetylamino-4-(4-fluoronaphth-1-yl)-6-isopropylpyrimidine, m.p. 115.4–116.7° C.

Similarly, 2-amino-4-(4-fluoronaphth-1-yl)-6-isopropylpyrimidine-1-N-oxide may be reacted with acetic anhydride to give directly the monoacetyl product of Formula I, 2-acetylamino-4-(4-fluoronaphth-1-yl)-6-isopropylpyrimidine-1-N-oxide, $^1$HNMR (200 MHz), J 1.39 (d,6h), 2.51(s,3H), 3.81(m,1H), 7.21–7.27(m,2H), 7.62–7.68(m,3H), 8.10–8.23(m,1H), 8.38–8.41(m,1H).

B. Preparation of I where R$^4$ and R$^5$ are Methanesulfonyl

2-Amino-4-(4-fluoronaphth-1-yl)-6-isopropylpyrimidine (0.374 g) was dissolved in dichloromethane (25 mL) and cooled to 0° C. Triethyl amine (0.5 mL) was added to the solution and methanesulfonyl chloride (0.12 mL) in dichloromethane (5 mL) was added dropwise. After stirring the mixture for 15 miutes, another portion of triethyl amine (0.25 mL) and methanesulfonyl chloride (0.12 mL) were added sequentially. After 15 minutes, the process was repeated and tlc examination showed a single new product. The reaction mixture was evaporated to dryness and purified by silica gel chromatography, eluting with ethyl acetate/hexane mixture. The colorless crystalline material was recrystallized from hexane-ether to afford 2-(bis-methanesulfonyl)amino-4-(4-fluoronaphth-1-yl)-6-isopropylpyrimidine, (354 mg), m.p. 143.8–144.2° C.

C. Preparation of I where $R^4$ is Methanesulfonyl and $R^5$ is Hydrogen

The 2-(bismethanesulfonyl)amino-4-(4-fluoronaphth-1-yl)-6-isopropylpyrimidine product from Example 10B above (0.204 g) was dissolved in methanol (5 mL) and treated at room temperature with 2.5N sodium hydroxide solution (0.2 mL). The reaction mixture was stirred at room temperature for 1 hour. The mixture was partitioned between 1N hydrochloric acid and ethyl acetate. The organic layer was dried over magnesium sulfate and evaporated to dryness and recrystallized to afford 2-(methanesulfonyl)amino-4-(4-fluoronaphth-1-yl)-6-isopropylpyrimidine as a crystalline material, m.p. 276–276.9° C. (prior decomposition at 273° C.).

D. Preparation of I where $R^4$ is Phenylamido and $R^5$ is Hydrogen

2-Amino-4-(4-fluoronaphth-1-yl)-6-isopropylpyrimidine (288.3 mg) was dissolved in benzene (50 mL) and phenyl isocyanate (119.1 mg) was added. The reaction mixture was heated to reflux for 48 hours, and the solvent was removed under vacuum. The residue was chromatographed on silica gel, eluting with hexane/ethyl acetate, to yield 1-[4-(4-fluoronaphth-1-yl)-6-isopropyl-pyrimidin-2-yl]-3-phenylurea (49.1 mg), m.p. 117–178° C.

EXAMPLE 12

Alternative Conversion of Compounds of Formula I where $R^1$ is Isopropyl, $R^3$ is 4-Fluoronaphth-1-yl, and $R^2$, $R^4$ and $R^5$ are Hydrogen to Other Compounds of Formula I, varying $R^2$ or $R^3$ A. Preparation of I where $R^2$ is Bromo and $R^3$ is 4-Fluoronaphth-1-yl To a solution of 2-amino-4-(4-fluoronaphth-1-yl)-6-isopropyl-pyrimidine (free base, 0.100 g) in carbon tetrachloride (10 mL) was added iron powder (0.002 g) and bromine (0.074 g) at room temperature. The reaction mixture was stirred at room temperature for 1 hour, after which time it was poured into sodium bicarbonate solution (saturated, 30 mL). The layers were separated and the aqueous layer was extracted three times with methylene chloride (3×10 mL). The combined organic layers were evaporated to dryness. The residue was purified by preparative thin layer chromatography, eluting with hexane/ethyl acetate, and recrystallized from ether/hexane to give 2-amino-5-bromo-4-(4-fluoronaphth-1-yl)-6-isopropyl-pyrimidine (0.072 g), m.p. 176–180° C.

B. Preparation of I where $R^2$ is Hydrogen and $R^3$ is 4-Thiomethylnaphth-1-yl 2-Amino-4-(4-fluoronaphth-1-yl)-6-isopropyl-pyrimidine (0.281 g) was dissolved in dimethyl sulphoxide (DMSO) (10 mL) and sodium thiomethoxide (0.070 g) was added. The reaction mixture was stirred at room temperature for 2 hours at which time another equivalent of thiomethoxide was added and the reaction stirred for another 2 hours. The mixture was poured into water (100 mL) and the product was extracted into ethyl acetate/hexane (3×50 mL). The combined organic extracts were dried over sodium sulfate and evaporated to dryness. The reaction product was purified by column chromatography on silica gel, eluting with hexane/ethyl acetate to give 2-amino-4-(4-methylthionaphth-1-yl)-6-isopropylpyrimidine (0.303 g), m.p. 139–140° C.

C. Preparation of I where $R^2$ is Hydrogen and $R^3$ is 4-Aminonaphth-1-yl

2-Amino-4-(4-fluoronaphth-1-yl)-6-isopropyl-pyrimidine (0.288 g) was dissolved in N-methy pyrrolidinone (5 mL) and sodium azide (0.288 g) was added. The mixture was brought to a temperature of 160° C. under an inert atmosphere for 16 hours. After cooling the reaction mixture was poured into water (50 mL) and the reaction product was extracted with ethyl acetate (3×30 mL). The organic layer was dried over sodium sulfate and evaporated to dryness. The product was purified by column chromatography on silica gel, eluting with hexane/ethyl acetate, and recrystallized from tert-butyl methyl ether to give 2-amino-4-(4-aminonaphth-1-yl)-6-isopropyl-pyrimidine (0.151 g), m.p. 185–186° C.

D. Similarly, replacing 2-amino-4-(4-fluoronaphth-1-yl)-6-isopropyl-pyrimidine with other compounds of Formula I, and following the procedures of Examples 12A, 12B, or 12C above, other compounds of Formula I are prepared.

EXAMPLE 13

Alternative Conversion of a Compound of Formula I where $R^1$ is Isopropyl, $R^2$ and $R^5$ are Hydrogen, $R^3$ is 4-Fluoronaphth-1-yl, and $R^4$ is 2-Aminoethyl to a Compound of Formula I, varying $R^4$ A. Preparation of I where $R^4$ is 2-(Methanesulfonamido)ethyl To a solution of 2-(2-aminoethyl)amino-4-(4-fluoronaphth-1-yl)-6-isopropylpyrimidine (0.170 g) dissolved diethyl ether was added dropwise a solution of methansulfonyl chloride (0.060 g) in ether. The reaction was carried out at room temperature, and after 1 hour the solvent was removed under reduced pressure. The crude material was taken up in methylene chloride and the free base was liberated by the addition of sodium carbonate solution. The organic layer was dried over magnesium sulfate and the reaction product isolated by evaporation, purified by column chromatography on silica gel, eluting with ethyl acetate/hexane to give 2-(2-methanesulfonamidoethyl)amino-4-(4-fluoronaphth-1-yl)-6-isopropylpyrimidine. The hydrochloride salt of the product was made (0.180 g), m.p. 85–91° C. (C 54.67%, H 5.59%, N 12.48%).

B. Similarly, replacing 2-(2-aminoethyl)amino-4-(4-fluoronaphth-1-yl)-6-isopropylpyrimidine with 2-(2-aminoethyl)amino-6-tert-butyl-4-(4-fluoronaphth-1-yl)-pyrimidine, and following the procedures of Examples 13A above, 6-tert-butyl-4-(4-fluoronaphth-1-yl)-2-(2-methanesulfonamidoethyl)amino-pyrimidine hydrochloride was prepared, m.p. 162.9–163.2° C.

C. Similarly, replacing 2-(2-aminoethyl)amino-4-(4-fluoronaphth-1-yl)-6-isopropylpyrimidine with other compounds of Formula I, and optionally replacing methanesulfonyl chloride with other sulfonyl chlorides, and following the procedures of Examples 13A above, other compounds of Formula I are prepared.

EXAMPLE 14

Alternative Conversion of a Compound of Formula I where $R^1$ is Isopropyl, $R^2$ and $R^5$ are Hydrogen, $R^3$ is 4-Fluoronaphth-1-yl, and $R^4$ is 2-Propionic acid methyl ester to a Compound of Formula I, varying $R^4$ A. 2-[6-Isopropyl-4-(4-fluoronaphth-1-yl)pyrimidin-2-ylamino]-propionic acid methyl ester was dissolved in ethanolic methyl amine solution (33%) and sonicated in a Branson ultrasonic bath for 3 hours. The solution was evaporated to dryness and taken up in methanol. Sufficient water was added to cause crystallization. The impure reaction product was further purified by silica gel column chromatography, eluting with methylene chloride/methanol and recrystallized from methanol/water to give 2-[6-isopropyl-4-(4-fluoronaphth-1-yl)pyrimidin-2-ylamino]-N-methyl-propionamide, m.p. 141.1–142.0° C.

B. Similarly, replacing 2-[6-isopropyl-4-(4-fluoronaphth-1-yl)pyrimidin-2-ylamino]-propionic acid methyl ester with 2-[6-Isopropyl-4-acenaphthen-5-yl)pyrimidin-2-ylamino]-propionic acid methyl ester, and following the procedures of Example 14A above, the compound 2-[6-isopropyl-4-acenaphthen-5-yl)pyrimidin-2-ylamino]-N-methyl-propionamide was prepared, m.p. 163–165° C.

C. Similarly, replacing 2-[6-Isopropyl-4-(4-fluoronaphth-1-yl)pyrimidin-2-ylamino]-propionic acid methyl ester with other compounds of Formula I, and optionally replacing methyl amine with other primary or secondary amines, and following the procedures of Examples 13A above, other compounds of Formula I are prepared.

EXAMPLE 15

Alternative Conversion of Compounds of Formula I where $R^4$ and $R^5$ are Hydrogen to Other Compounds of Formula I where $R^4$ is 2-Propionic acid methyl ester and $R^5$ is Hydrogen Compounds of Formula I where $R^4$ and $R^5$ are hydrogen may be converted to other compounds of Formula I where $R^4$ is 2-propionic acid methyl ester and $R^5$ is hydrogen, following the procedures described in Alcaide, Benito et al., J. Org. Chem. 1990, 55, 3143–3147):

2-(6-isopropyl-4-(4-fluoronaphth-1-yl)-pyrimidin-2-ylamino)-propionic acid methyl ester maleate, m.p. 123.7–124.5° C.;

2-(6-isopropyl-4-(4-fluoronaphth-1-yl)-pyrimidin-2-ylamino)-propionic acid, m.p. 175.6–176.3° C.; and 2-(4-acenaphthen-5-yl-6-isopropyl-pyrimidin-2-ylamino)-propionic acid methyl ester, m.p. 87.5–93.2° C.

EXAMPLE 16

This example illustrates the preparation of a representative pharmaceutical formulation for oral administration containing an active compound of Formula I, e.g., 2-amino-4-(4-fluoronaphth-1-yl)-6-isopropylpyrimidine.

| Ingredients | Quantity per tablet, mgs. |
| --- | --- |
| Active Compound | 200 |
| Lactose, spray-dried | 148 |
| Magnesium stearate | 2 |

The above ingredients are mixed and introduced into a hard-shell gelatin capsule.

Other compounds of Formula I, such as those prepared in accordance with Examples 1–15, can be used as the active compound in the preparation of the orally administrable formulations of this example.

EXAMPLE 17

This example illustrates the preparation of another representative pharmaceutical formulation for oral administration containing an active compound of Formula I, e.g., 2-amino-4-(4-fluoronaphth-1-yl)-6-isopropylpyrimidine.

| Ingredients | Quantity per tablet, mgs. |
| --- | --- |
| Active Compound | 400 |
| Cornstarch | 50 |
| Lactose | 145 |
| Magnesium stearate | 5 |

The above ingredients are mixed intimately and pressed into single scored tablets.

Other compounds of Formula I, such as those prepared in accordance with Examples 1–15, can be used as the active compound in the preparation of the orally administrable formulations of this example.

EXAMPLE 18

This example illustrates the preparation of a representative pharmaceutical formulation containing an active compound of Formula I, e.g., 2-amino-4-(4-fluoronaphth-1-yl)-6-isopropylpyrimidine.

An oral suspension is prepared having the following composition:

| Ingredients | | |
| --- | --- | --- |
| Active Compound | | 1.0 g |
| Fumaric acid | | 0.5 g |
| Sodium chloride | | 2.0 g |
| Methyl paraben | | 0.1 g |
| Granulated sugar | | 25.5 g |
| Sorbitol (70% solution) | | 12.85 g |
| Veegum K (Vanderbilt Co.) | | 1.0 g |
| Flavoring | | 0.035 ml |
| Colorings | | 0.5 mg |
| Distilled water | q.s. to | 100 ml |

Other compounds of Formula I, such as those prepared in accordance with Examples 1–15, can be used as the active compound in the preparation of the orally administrable formulations of this example.

EXAMPLE 19

This example illustrates the preparation of a representative pharmaceutical formulation for oral administration containing an active compound of Formula I, e.g., 2-amino-4-(4-fluoronaphth-1-yl)-6-isopropylpyrimidine.

An injectable preparation buffered to a pH of 4 is prepared having the following composition:

| Ingredients | | |
| --- | --- | --- |
| Active Compound | | 0.2 g |
| Sodium Acetate Buffer Solution (0.4M) | | 2.0 ml |
| HCL (1N) | q.s. to | pH 4 |
| Water (distilled, sterile) | q.s. to | 20 ml |

Other compounds of Formula I, such as those prepared in accordance with Examples 1–15, can be used as the active compound in the preparation of the injectable formulations of this example.

EXAMPLE 20

This example illustrates the preparation of a representative pharmaceutical formulation for topical application containing an active compound of Formula I, e.g., 2-amino-4-(4-fluoronaphth-1-yl)-6-isopropylpyrimidine.

| Ingredients | | grams |
|---|---|---|
| Active compound | | 0.2–10 |
| Span 60 | | 2 |
| Tween 60 | | 2 |
| Mineral oil | | 5 |
| Petrolatum | | 10 |
| Methyl paraben | | 0.15 |
| Propyl paraben | | 0.05 |
| BHA (butylated hydroxy anisole) | | 0.01 |
| Water | q.s. to | 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Examples 1–15, can be used as the active compound in the preparation of the topical formulations of this example.

EXAMPLE 21

This example illustrates the preparation of a representative pharmaceutical formulation containing an active compound of Formula I, e.g., 2-amino-4-(4-fluoronaphth-1-yl)-6-isopropylpyrimidine.

A suppository totalling 2.5 grams is prepared having the following composition:

| Ingredients | |
|---|---|
| Active Compound | 500 mg |
| Witepsol H-15* | balance |

(*triglycerides of saturated vegetable fatty acid; a product of Riches-Nelson, Inc., New York, N.Y.)

Other compounds of Formula I, such as those prepared in accordance with Examples 1–15, can be used as the active compound in the preparation of the suppository formulations of this example.

EXAMPLE 22

Cloned Rat 5-HT2B Receptor Binding Assay

The following describes an in vitro binding assay utilizing cloned 5-HT$_{2B}$ receptors radiolabelled with [$^3$H]-5HT.

Mouse NIH3T3 fibroblasts expressing cloned 5-HT2B receptor were maintained in Dulbecco's Modified Eagle medium with 10% Fetal Calf Serum and 250 μg/mL G418 in 95/5% O$_2$/CO$_2$. The cells were harvested using 2 mM EDTA in phosphate buffered saline (calcium/magnesium free) and centrifuged (500 g). The cell pellet was homogenized using a Polytron P10 disrupter (setting 5, 5 sec) in homogenization buffer (Tris, 50 mM; Na$_2$EDTA, 5 mM) and the homogenate was centrifuged at 19,500 rpm using a Sorvall/Dupont RC5C centrifuge with an SS34 rotor (30,000–48,000 g, 15 minutes). The pellet was homogenized (setting 5, 5 sec) in homogenization buffer and the homogenate was centrifuged (30,000–48,000 g, 15 minutes). The pellet was homogenized (setting 5, 5 sec) in resuspension buffer (Tris, 50 mM; EDTA 0.5 mM) and the homogenate was centrifuged (30,000–48,000 g, 15 minutes). The pellet was homogenized (setting 5, 5 sec) in a small volume of resuspension buffer to give approximately 1.5×10$^8$ cells/mL.

The membranes were separated into 1 mL aliquots and stored at −70° C.

The membranes were thawed at room temperature and diluted with assay buffer calcium chloride-2H$_2$O, 4.5 mM; Tris, 50 mM; 0.1% ascorbic acid). Specific binding is at least 90% of total binding with 1.5×10$^6$ cells per assay tube. The membranes were homogenized (setting 5, 5 sec) and then the homogenate was added to assay tubes containing [$^3$H]-5HT (2×10$^{-10}$M) test compound (1×10$^{-10}$–1×10$^{-4}$M) and assay buffer (q.s. to 500 μL). The assay mixture was incubated at 40° C. for 2 hours and then filtered over 0.1% polyethyleneimine pre-treated glass fiber filtermats using a Brandel cell harvester. The assay tubes were rinsed with cold assay buffer and dried by drawing air over the filter for 10 seconds. Radioactivity retained on the filters was determined by liquid scintillation counting. For each compound tested the concentration producing 50% inhibition of binding (IC$_{50}$) was determined using iterative curve fitting techniques.

Proceeding as in Example 22, the compounds of the invention were found to have affinity for the 5-HT$_{2B}$ receptor.

EXAMPLE 23

5-HT$_{2A}$ 5-HT$_{2B}$ 5HT$_{2C}$ Receptor Binding Methods

The following describes receptor binding methods in which ligands with high affinity for 5-HT$_{2B}$ receptors were counter screened at 5-HT$_{2A}$ and 5-HT$_{2C}$ receptors to demonstrate selectivity.

5-HT$_{2A}$ receptors were labelled with [$^3$H]ketanserin in human cortex, in Cos-7 cells expressing a cloned human 5-HT$_{2A}$ receptor and in NIH-3T3 cells expressing the rat 5-HT$_{2A}$ receptor. For competition binding studies the ligand concentration was approximately 0.1 nM. For saturation binding studies concentrations of radioligand ranged from 0.01 nM to 2.0 nM. Assays were conducted in 0.5 mL of assay buffer containing 50 mM Tris-HCl, 4 mM calcium chloride, and 0.1% ascorbic acid (pH 7.4 at 4° C.). Non-specifc binding was defined with 10 mM unlabelled ketanserin. After a 60 minute incubation at 32° C., membranes were harvested onto filters treated with 0.1% polyethylenimine and the bound radioactivity was determined.

Human 5-HT$_{2B}$ receptors were labelled in Cos-7 cells as described above. except that the radioligand was [$^3$H]5-HT and that the assay buffer contained 10 mM pargyline and 0.1% ascorbic acid. For competition binding studies the radioligand concentration was approximately 0.4 nM while for saturation binding studies the concentration of [$^3$H]5-HT ranged from 0.05 to 8 nM. Non-specific binding was defined with 10 mM 5-HT. Incubations were for 120 minutes at 4° C.

5-HT$_{2C}$ receptors were labelled in choroid plexus, Cos-7 cells expressing the human 5-HT 2C receptor and in NIH-3T3 expressing the rat 5-HT$_{2A}$ receptor.

Assays were conducted as described for the 5-HT$_{2A}$ receptor except that the radioligand was [$^3$H]mesulergine. The radioligand concentration for competition studies was approximately 0.2 nM while for saturation binding studies the concentration ranged from 0.1 to 18 nM. Non-specific binding was defined with 10 μM unlabelled mesulergine.

Competition radioligand binding data was analyzed using a four parameter logistic equation and iterative curve-fitting techniques to obtain estimates of the IC$_{50}$ and Hill slope. Kd values, determined from saturation binding studies were then used to calculate inhibition dissociation constants (Ki).

Proceeding as in Example 23, the compounds of the invention were found to have affinity for the 5-HT$_{2B}$ receptor.

EXAMPLE 24

5-HT$_{2B}$ Receptor Tissue Based Functional Assay

The following describes an in vitro functional assay characterizing 5-HT receptors (the putative 5-HT$_{2B}$) in rat stomach fundus longitudinal muscle (Baxter et al., *Brit. J. Pharmacol.* 1994, 112, 323–331).

Strips of longitudinal muscle were obtained from the stomach fundus of male Sprague Dawley rats. The mucosa was removed and the strips were suspended with a resting tension of 1 gram in oxygenated (95% O$_2$/5% CO$_2$) Tyrode solution at 37° C. The composition of the Tyrode solution was as follows (mM): NaCl 136.9; KCl 2.7; NaH$_2$PO$_4$ 0.4; MgCl$_2$ 1.0; glucose 5.6; NaHCO$_3$ 11.9; CaCl$_2$ 1.8.

Concentration-response curves to 5-HT receptor agonists were constructed under conditions where cyclooxygenase activities were inactivated by 3 μM indomethacin, monoamine oxidase activities inactivated by 0.1 mM pargyline, and uptake mechanisms inactivated by 30 μM cocaine and 30 μM corticosterone.

Effects of drugs were monitored by tension transducers and recorded on polygraph recorders. Tissue response was measured as changes in isometric tension (g). The mean potency (EC$_{50}$) and maximum response were evaluated by standard iterative curve fitting procedures.

Effects of antagonists were determined by measuring dextral shifts to the agonist concentration-response curve after equilibration of the antagonists for at least 1 hour. Concentration-ratios were measured at half maximal response levels and single concentration antagonist affinities were determined by the equation:

KB=[Antagonist concentration] /(Concentration ratio−1) Schild regression analysis was employed with multiple antagonist concentrations when the compound showed competitive behavior.

Proceeding as in Example 24, the compounds of the present invention were found to be antagonists at the 5-HT$_{2B}$ receptor.

EXAMPLE 25

Anxiolytic Behavior Assay

The following describes an in vivo method for determining anxiolytic activity by measuring the extent the drug affects the natural anxiety of mice when exposed to a novel, brightly lighted environment.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin 1980, as described in Kilfoil et al., cited previously. Briefly, the chamber consists of a plexiglass box (44×21×21 cm), divided into two chambers by a black plexiglass partition. The partition dividing the two chambers contains a 13'5 cm opening through which the mouse can easily pass. The dark chamber has clear sides and a white floor.

A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is reflected by increased latency (the time for the mouse to move to the dark chamber when first placed in the center of the lighted area), increase in shuttle activity, increased or unaltered locomotor activity (number of grid lines crossed) and decreased time spent in the dark compartment.

Proceeding as in Example 25, the compounds of the present invention were found to ameliorate anxiolytic behavior.

EXAMPLE 26

Withdrawal Anxiety Assay

The following describes an in vivo procedure for determining amelioration of the symptoms caused by withdrawal from addictive substances by measuring the extent the drug affects the anxiety that occurs in mice after chronically treating with an addictive substance and then abruptly ceasing the treatments.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 14). Anxiolysis is seen as a general increase in exploratory activity in the lighted area. An increase in exploratory activity is reflected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0% w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the ethanol, cocaine or nicotine treatment is ceased.

Proceeding as in Example 26, the compounds of the present invention were found to show amelioration of the symptoms caused by withdrawal from addictive substances.

EXAMPLE 27

Pain Assay

The following describes an in vivo procedure for determining the amelioration of pain, particularly inflammatory pain, by measuring the effect of the compound(s) of the present invention on the carrageenan paw pressure assay response in rats.

Male Sprague Dawley rats are maintained with free access to food and water for at least seven (7) days prior to use. The rats are weighed and randomly assigned to treatment groups. A 1% solution of Carrageenan Lambda (Gelatin, vegetable; Irish Moss) Type IV is prepared in normal saline. Indomethacin is used as a reference substance. The vehicle used is 10% DMSO, 50% proplyene glycol, and 40% water.

The rats (10 per group) are dosed i.p. with vehicle/saline (2 ml/kg), vehicle/carrageenan (2 ml/kg), indomethacin (6 mg/kg), or a compound of the present invention (0.3 mg/kg, 1 mg/kg, or 3 mg/kg). The rats are lightly anesthetized with halothane and 1% carrageenan is injected into the left hindpaw (intraplantar). The amount of force applied to the left hindpaw of each rat is tested using an analgesy-meter three (3) hours after the carrageenan injection.

Proceeding as in Example 27, the mean withdrawal pressure (in grams) of each of the treatment groups was obtained to determine the effect on paw hyperalgesia. Carrageenan induced a painful inflammatory response in the rats, as indicated by the lower mean withdrawal pressure compared with the rats administered vehicle/saline. Compounds of the present invention were found to ameliorate the pain symptoms associated with carrageenan administration, as indicated by a significantly increased mean withdrawal pressure comparable to the mean withdrawal pressure of the rats administered vehicle/saline.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for treating a mammal having a disease state which is alleviable by treatment with a 5-HT$_{2B}$ antagonist, which comprises administering to a mammal in need thereof a therapeutically effective amount of a compound of the formula:

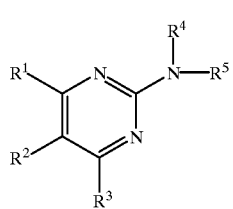

(I)

wherein:

$R^1$ is hydrogen, alkyl, lower alkoxy, hydroxyalkyl, cycloalkyl, cycloalkyl lower alkyl, alkenyl, lower thioalkoxy, halo, fluoroalkyl, —NR$^6$R$^7$, —CO$_2$R$^8$, —O(CH$_2$)$_n$R$^9$, or lower alkyl optionally substituted with hydroxy, alkoxy, halo, or aryl;

in which n is 1, 2, or 3;

$R^6$ and $R^7$ are hydrogen or lower alkyl;

$R^8$ is hydrogen or lower alkyl; and $R^9$ is hydrogen, lower alkyl, hydroxy, hydroxy lower alkyl, lower alkenyl, or lower alkoxy;

$R^2$ is hydrogen, lower alkyl, lower alkoxy, halo, or lower fluoroalkyl;

$R^3$ is optionally substituted aryl other than pyridyl, thienyl, or furanyl;

$R^4$ is hydrogen, lower alkyl, cycloalkyl, alkenyl, acyl, amino, amido, aryl, —(CH$_2$)$_m$NR$^{10}$R$^{11}$, or lower alkyl optionally substituted by amino, monosubstituted amino, disubstituted amino, hydroxy, carboxy, aryl, lower alkoxy, amido, alkoxy carbonyl, tetrahydrofuran-2-yl, hydroxyalkoxy, or sulfonamido;

in which $R^{10}$ and $R^{11}$ are hydrogen or lower alkyl; and $R^5$ is hydrogen or lower alkyl;

provided that:
(i) when $R^3$ is naphthyl, indol-1-yl, or 2,3-dihydroindol-1-yl, and $R^2$, $R^4$ and $R^5$ are all hydrogen, $R^1$ is not methyl;
(ii) when $R^3$ is phenyl or naphthyl, $R^1$ is not —NR$^6$R$^7$;
(iii) when $R^3$ is phenyl, $R^2$ is not lower alkoxy, and $R^1$ and $R^2$ are not halo;
(iv) when $R^3$ is phenyl and $R^1$ is H, $R^2$ is not methyl; and
(v) when $R^3$ is 1,2,3,4-tetrahydroquinolinyl, $R^4$ and $R^5$ are hydrogen;

or a pharmaceutically acceptable salt or N-oxide thereof.

2. The method of claim 1, wherein the disease state comprises pain.

3. The method of claim 2, wherein the disease state comprises inflammatory pain.

4. The method of claim 2, wherein the disease state comprises neuropathic pain.

5. The method of claim 2, wherein the disease state comprises cancer pain.

6. The method of claim 2, wherein the disease state comprises acute pain.

7. The method of claim 2, wherein the disease state comprises chronic pain.

* * * * *

UNITED STATES PATENT AND TRADEMARK OFFICE
CERTIFICATE OF CORRECTION

PATENT NO. : 5,958,934
DATED : September 28, 1999
INVENTOR(S) : Berger et al

It is certified that error appears in the above-identified patent and that said Letters Patent is hereby corrected as shown below:

In Claim 1 column 56, line 21, delete "-$(CH_2)_mNR^{10}R^{11}$,";

In Claim 1, column 56, lines 27 and 28, delete "in which $R^{10}$ and $R^{11}$ are hydrogen or lower alkyl;".

Signed and Sealed this

Twenty-third Day of May, 2000

*Attest:*

Q. TODD DICKINSON

*Attesting Officer*       *Director of Patents and Trademarks*